United States Patent
Johns et al.

(10) Patent No.: US 9,169,329 B2
(45) Date of Patent: Oct. 27, 2015

(54) ANTIBODIES DIRECTED TO THE RECEPTOR TYROSINE KINASE C-MET

(75) Inventors: Terrance Grant Johns, Box Hill North Victoria (AU); Ermanno Gherardi, Pavia (IT); Andrew Mark Scott, Kew East Victoria (AU)

(73) Assignees: Ludwig Institute for Cancer Research, New York, NY (US); Monash University, Clayton, Victoria (AU)

( * ) Notice: Subject to any disclaimer, the term of this patent is extended or adjusted under 35 U.S.C. 154(b) by 114 days.

(21) Appl. No.: 13/701,151

(22) PCT Filed: Jun. 1, 2011

(86) PCT No.: PCT/AU2011/000681
§ 371 (c)(1),
(2), (4) Date: Feb. 19, 2013

(87) PCT Pub. No.: WO2011/150454
PCT Pub. Date: Dec. 8, 2011

(65) Prior Publication Data
US 2013/0171063 A1 Jul. 4, 2013

Related U.S. Application Data

(60) Provisional application No. 61/396,691, filed on Jun. 1, 2010.

(30) Foreign Application Priority Data

Nov. 3, 2010 (AU) ................................ 2010904903

(51) Int. Cl.
*C07K 16/40* (2006.01)
*A61K 39/395* (2006.01)
*G01N 33/74* (2006.01)
*C07K 16/28* (2006.01)
*A61K 45/06* (2006.01)
*C07K 14/705* (2006.01)

(52) U.S. Cl.
CPC .......... *C07K 16/40* (2013.01); *A61K 39/39558* (2013.01); *A61K 45/06* (2013.01); *C07K 14/705* (2013.01); *C07K 16/2803* (2013.01); *G01N 33/74* (2013.01); *C07K 2317/34* (2013.01); *C07K 2317/56* (2013.01); *C07K 2317/73* (2013.01); *C07K 2317/76* (2013.01)

(58) Field of Classification Search
CPC .............. C07K 16/2803; C07K 16/40; C07K 2317/76; C07K 2317/24; A61K 39/39558; G01N 33/74
See application file for complete search history.

(56) References Cited

U.S. PATENT DOCUMENTS

| | | | |
|---|---|---|---|
| 2007/0098707 A1* | 5/2007 | Kong-Beltran et al. | 424/94.2 |
| 2009/0053737 A1* | 2/2009 | Cao (Brian) et al. | 435/7.4 |
| 2010/0016241 A1 | 1/2010 | Kong-Beltran et al. | |
| 2010/0129369 A1* | 5/2010 | Davies et al. | 424/138.1 |

FOREIGN PATENT DOCUMENTS

| | | |
|---|---|---|
| EP | 2014681 | 1/2009 |
| EP | 2554993 | 2/2013 |
| WO | 2003057155 | 7/2003 |
| WO | 2005016382 | 2/2005 |
| WO | WO2006015371 | 2/2006 |
| WO | 2007126799 | 11/2007 |
| WO | 2009007427 | 1/2009 |
| WO | WO2009029591 | 3/2009 |
| WO | 2010037835 | 4/2010 |

OTHER PUBLICATIONS

Almagro & Fransson, Frontiers in Bioscience 2008; 13:1619-33.*
PJ Carter, Nat Rev Immunol, 2006; 6:343-357.*
Birchmeier, C et al (2003) Met, metastasis, motility and more Nat Rev Mol Cell Biol 4(12):915-925.
Burgess, T et al (2006) Fully human monoclonal antibodies to hepatocyte growth factor with therapeutic potential against hepatocyte growth factor/c-Met-dependent human tumors Cancer Res 66(3):1721-1729.
Cipriani, NA et al (2009) MET as a target for treatment of chest tumors Lung Canc 63(2):169-179.
Comoglio, PM et al (2008) Drug development of MET inhibitors: targeting oncogene addiction and expedience Nat Rev Drug Discov 7(6):504-516.
Corso, S et al (2005) Cancer therapy: can the challenge be MET? Trends Mol Med 11(6):284-292.
Eder, JP et al (2009) Novel Therapeutic Inhibitors of the c-Met Signaling Pathway in Cancer Clin Cancer Res 15(7):2207-2214.
Engelman, JA et al (2007) MET amplication leads to gefitinib resistance in lung cancer by activating ERBB3 signalling Science 316(5827):1039-1043.
Faletto, DL et al (1992) Evidence for non-covalent clusters of the c-met proto-oncogene product Oncogene 7 (6):1149-1157.
Gentile, A et al (2008) The Met tyrosine kinase receptor in development and cancer Cancer Metastasis Rev 27:85-94.
Gherardi, E et al (2003) Functional map and domain structure of MET, the product of the c-met protoconcogene and receptor for hepatocyte growth factor/scatter factor Proc Natl Acad Sci USA 100(21):12039-12044.
Gomes, DA et al (2008) c-Met must translocate to the nucleus to initiate calcium signals J Biol Chem 283:4344-4351.
Hay, RV et al (2003) Radioimmunoscintigraphy of human met-expressing tumor xenografts using met3, a new monoclonal antibody Clin Cancer Res 9(10 Pt 2):3839S-3844S.
Hay, RV et al (2005) Nuclear imaging of Met-expressing human and canine cancer xenografts with radiolabeled monoclonal antibodies (MetSeek) Clin Cancer Res 11(19 Pt 2):7064s-7069s.

(Continued)

*Primary Examiner* — Sheela J Huff
*Assistant Examiner* — Jessica H Roark
(74) *Attorney, Agent, or Firm* — Klauber & Jackson LLC

(57) ABSTRACT

The present invention relates to antibodies that specifically bind to unprocessed c-Met present on the surface of tumor cells. These antibodies are useful in the diagnosis and treatment of cancer or as agents for delivering moieties to cancer cells. The antibodies of the present invention may also be used in therapy in combination with chemotherapeutics or anti-cancer agents.

20 Claims, 9 Drawing Sheets

(56) References Cited

OTHER PUBLICATIONS

Jagadeeswaran, R et al (2006) Functional analysis of c-Met/hepatocyte growth factor pathway in malignant pleural mesothelioma Cancer Res 66(1):352-361.

Kermorgan, S et al (2003) Protein kinase C controls microtubule-based traffic but not proteasomal degradation of c-Met J Biol Chem 278(31):28921-28929.

Knudsen, BS et al (2009) A novel multipurpose monoclonal antibody for evaluating human c-Met expression in preclinical and clinical settings Appl Immunohistochem Mol Morphol 17:57-67.

Komada, M et al (1993). Proteolytic processing of the hepatocyte growth factor/scatter factor receptor by furin FEBS Letters 328:25-29.

Kong, DS et al (2009) Prognostic significance of c-Met expression in glioblastomas Cancer 115(1):140-148.

Ma, PC et al (2003) C-Met:structure, functions and potential for therapeutic inhibition Cancer Metastasis Rev 22:309-325.

Ma, PC et al (2003) c-Met mutational analysis in small cell lung cancer:novel juxtamembrane domain mutations regulating cytoskeletal functions Cancer Res 63(19):6272-6281.

Martens, T et al (2006) A novel one-armed anti-c-Met antibody inhibits glioblastoma growth in vivo Clin Cancer Res 12 (20 Pt 1):6144-6152.

McLendon, R et al (2008) Comprehensive genomic characterisation defines human glioblastoma genes and core pathways Nature 455(7216):1061-1068.

Mizuno, K et al (1993) Cell density-dependent regulation of hepatocyte growth factor receptor on adult rat hepatocytes in primary culture J Biochem 114(1):96-102.

Mondino, A et al (1991). Defective posttranslational processing activates the tyrosine kinase encoded by the MET proto-oncogene (hepatocyte growth factor receptor) Mol Cell Biol 11(12):6084-6092.

Nguyen, TH et al (2003) Improved gene transfer selectivity to hepatocarcinoma cells by retrovirus vector displaying single-chain variable fragment antibody against c-Met Cancer Gene Ther 10(11):840-849.

Ohashi, K et al (2000) Nat Med 6(3):327-331.

Olivero, M et al (1996) Overexpression and activation of hepatocyte growth factor/scatter factor in human non-small-cell lung carcinomas Br J Cancer 74(12):1862-1868.

Petrelli, A et al (2006) Ab-induced ectodomain shedding mediates hepatocyte growth factor receptor down-regulation and hampers biological activity Proc Natl Acad Sci USA 103(13):5090-5095.

Pillay, V et al (2009) The plasticity of oncogene addiction: implications for targeted therapies directed to receptor tyrosine kinases Neoplasia 11(5):448-458.

Prat, M et al (1991) C-Terminal truncated forms of met, the hepatocyte growth factor receptor Mol Cell Biol 11 (12):5954-5962.

Prat, M et al (1998) Agonistic monoclonal antibodies against the Met receptor dissect the biological responses to HGF J Cell Sci 111(pt 2):237-247.

Puri, N. et al (2007) c-Met is a potentially new therapeutic target treatment for human melanoma Clin Cancer Res 13 (7):2246-2253.

Rodrigues, GA et al (1991) Alternative splicing generates isoforms of the met receptor tyrosine kinase which undergo differential processing Mol Cell Biol 11(6):2962-2970.

Rong, S et al (1992) Tumorigenicity of the met proto-oncogene and the gene for hepatocyte growth factor Mol Cell Biol 12(11):5152-5158.

Ruco, LP et al (1996) Expression of Met protein in thyroid tumours J Pathol 180(3):266-270.

Salgia, R (2009) Role of c-Met in cancer: emphasis on lung cancer Semin Oncol 36(2 Suppl 1): S52-S58.

Stellrecht, CM et al (2009) MET receptor tyrosine kinase as a therapeutic anticancer target Cancer Lett 280(1):1-14.

Tseng, JR et al (2008) Preclinical efficacy of the c-Met inhibitor CE-355621 in a U87 MG mouse xenograft model evaluated by 18F-FDG small-animal PET J Nucl Med 49(1):129-134.

Van der Horst, EH et al (2009) Discovery of fully human anti-MET monoclonal antibodies with anti-tumor activity against colon cancer tumor models in vivo Neoplasia 11(4):355-364.

Zhu, J et al (2006) Affinity maturation and characterization of Internalized human anti-met recombinant antibody Fab Prog in Biochem & Biophysics 34(1):73-79, Abstract Only.

Goetsch, L et al (2010) Abstract 2448: h224G11, a humanized whole antibody targeting the c-Met receptor, induces c-Met down-regulation and triggers ADCC functions.

Michaud, NR et al (2012) Biochemical and pharmacological characterization of human c-Met neutralizing monoclonal antibody CE-355621 MAbs 4(6):710-723.

* cited by examiner

A

B

C

ANTIBODIES DIRECTED TO THE RECEPTOR TYROSINE KINASE C-MET

CROSS REFERENCE TO RELATED APPLICATIONS

The present application is a National Stage Application claiming the priority of co-pending PCT Application No. PCT/AU2011/000681 filed Jun. 1, 2011, which in turn claims priority from Australian Application No. 2010904903 filed Nov. 30, 2010, which in turn claims priority from U.S. Provisional Application No. 61/396,691 filed Jun. 1, 2010. Applicants claim the benefits of 35 U.S.C. §120 as to the PCT application and priority under 35 U.S.C. §119 as to the said Australian application and U.S. Provisional application, and the entire disclosures of both applications are incorporated herein by reference in their entireties.

FIELD OF THE INVENTION

The present invention relates to antibodies that specifically bind to the alpha or beta chain of c-Met. These antibodies are useful in the diagnosis and treatment of cancer or as agents for delivering moieties to cancer cells. The antibodies of the present invention may also be used in therapy in combination with chemotherapeutics or anti-cancer agents.

BACKGROUND OF THE INVENTION

Receptor tyrosine kinases (RTKs) mediate intercellular signals which are essential for the development and maintenance of cells of multicellular organisms. The minimal domain structure of RTKs consists of an extracellular ligand-binding domain structure, a single transmembrane helix, and a cytoplasmic tyrosine kinase (TK) domain.

c-Met (mesenchymal-epithelial transition factor) is a cell surface, disulphide linked heterodimeric RTK encoded by the c-met protooncogene. The c-Met receptor is also referred to as hepatocyte growth factor receptor (HGFR). It is the receptor for hepatocyte growth factor/scatter factor (HGF/SF) which is a large polypeptide growth factor discovered as a protein causing dispersion of epithelial colonies and cell migration (SF) and as a liver mitogen (HGF).

The c-Met receptor is synthesized as a 170 kDa precursor which is glycosylated and proteolytically cleaved in the post-Golgi compartment into an extracellular 50 kDa α-chain and an extracellular/intracellular 145 kDa β-chain that contains the TK domain. The chains remain associated after cleavage due to a disulfide linkage resulting in a heterodimeric molecule. The HGF/SF and heparin-binding sites of c-Met are contained within a large N-terminal domain spanning the alpha chain (amino acids 25-307) and the first 212 amino acids of the beta chain (amino acids 308-519). Within residues 520-561 is a cysteine-rich domain. Neither this domain, nor the C-terminal half of c-Met (amino acids 562-932) bind HGF/SF or heparin directly.

The extracellular portion of c-Met contains a region of homology to semaphorins (Sema domain, which includes the full alpha chain and the N-terminal part of the beta chain of c-Met), a cysteine-rich c-Met related sequence (MRS) followed by glycine-proline-rich (G-P) repeats, and four immunoglobulin-like structures. The intracellular region of c-Met contains three region: (i) a juxtamembrane segment that contains (a) a serine residue (Ser 985) that, when phosphorylated by protein kinase C or by $Ca^{2+}$ calmodulin-dependent kinases downregulates the receptor kinase activity; and (b) a tyrosine (Tyr 1003) that binds the ubiquitin ligase Cbl responsible for Met polyubiquitination, endocytosis and degradation; (ii) a tyrosine kinase domain that, upon receptor activation, undergoes transphosphorylation on Tyr1234 and Tyr1235; and (iii) the C-terminal region, which comprises two crucial tyrosines (Tyr1349 and Tyr1356) inserted in a degenerate motif that represents a multi-substrate docking site capable of recruiting several down stream adaptors containing Src homology-(SH2) domains. A detailed review of the structure can be found in, Gentile, A et al., (2008).

c-Met Expression and Signaling

Typically c-Met expression is found in epithelial derived cells while HGF/SF is expressed in the surrounding mesenchyme. During development, c-Met is required for proper development of the placenta, liver, kidney, neuronal and skeletal muscle. In adults, c-Met expression plays a role in hematopoiesis, including B-cell development during antigen selection, and is upregulated during tissue injury.

Upon HGF binding, c-Met homodimerises which leads to the activation of its TK domain, as well as autophosphorylation of several tyrosine residues including the C-terminal residues Y1349 and Y1356. Phosphorylated Y1349 and Y1356 form a multi-substrate docking site ($Y^{1349}VHVXXXY^{1356}VNV$) (SEQ ID NO:43) capable of binding several adaptor proteins to initiate downstream signaling, commonly using the PI3K/Akt and Ras/MAPK pathways (Eder J P et al., 2009, and Birchmeier C et al., 2003). The multi-substrate docking site is an absolute requirement for c-Met signaling.

The juxtamembrane domain of c-Met also plays a regulatory role. Phosphorylation of $Y^{1003}$ in this domain is involved in c-Met downregulation as it binds proteins such as the E3 ubiquitin ligase, CBL. Binding of CBL also leads to the recruitment of the endophilin-CIN85 complex, resulting in c-Met internalization and degradation (Ma et al., 2003). Phosphorylation of $S^{975}$ in the juxtamembrane domain is also involved in c-Met internalization and has been shown to be phosphorylated by protein kinase C and $Ca^{2+}$-calmodulin-dependent kinase. The internalization of c-Met is necessary for ERK signaling.

In addition to ligand activation of c-Met, there is also signal induction from cross-talk between c-Met and other receptors. In tumor cells, c-Met co-immunoprecipitates with EGFR regardless of the presence of their ligands.

Role of c-Met in Cancer

The c-Met receptor tyrosine kinase is involved in multiple pathways linked to cancer, such as cell migration, invasion, proliferation and angiogenesis, and is upregulated in a large number of cancers (Christensen, J G et al., (2005) Cancer Let 225: 1-26; Jiang, W G et al., (2005) Crit Rev Oncol Hematol 53:35-69). c-Met was first identified as an oncogene in 1984 and is among the most frequently expressed oncogenes in human cancer. C-Met alterations or deregulation (mutations, altered expression, amplification) has been associated with many types of human cancers, including kidney, liver, stomach, colon, breast, brain, prostate, ovarian, lung, bladder, head and neck, thyroid (Birchmeier, C et al., (2003) Cell Biol 4:915-925; Corso S et al., (2005) Trends Mol Med 11:284-92; Christensen J G., et al (2005) Cancer Lett 225:1-26; Salgia, R (2009) Semin Oncol 36(2 Suppl 1) S52-58; Engelman J A., et al (2007) Science 316:1039-1043; vai.org/vari/met and cancer). Genetic alterations which generate ligand-independent c-Met mutants have been found in both hereditary and sporadic papillary renal cell carcinomas and involve mutations in the tyrosine kinase domain of c-Met (Schmidt L et al., (1997) Nat Genet 16:68-73; Schmidt L et al., (1999) Oncogene 18:2343-50; Dharmawardana P G et al., (2004) Curr Mol Med 4:855-68). Missense mutations in c-Met (primarily in the kinase domain) have also been identified in ovarian cancer, childhood hepatocellular carcinoma, metastatis head and neck squamous cell carcinomas, and gastric cancer (Gentile et al., 2008; Ma et al., 2003). In melanoma and thoracic malignancies such as small cell lung cancer and mesothelioma, c-Met mutations clustered predominantly in the SEMA and juxtamembrane domains (Ma P C et al., 2003, Puri N et al., 2007 and Jagadeeswaran R et al., 2006).

The most common genetic alteration involving c-Met is gene amplification leading to c-Met over-expression. c-Met overexpression has been found in a large number of human tumors including breast, gastric, cervix, hepatocellular, brain and head and neck cancers (www.vai.org/met) and may also lead to ligand-independent kinase activation. Approximately 25% of ovarian cancers and 11% of gliomas express high levels of c-Met. Most often in cancer, c-Met activation occurs via a ligand-dependent mechanism. This stimulation is often autocrine as is typically seen in glioblastoma and multiple myeloma.

The HGF:c-Met signaling axis has an important role in the initiation and progression of several aggressive cancers such as glioblastoma multiforme (GBM), a lethal tumor of the brain which is refractory to currently available therapies. While the c-met gene is amplified in approximately 4% of GBM (McLendon R et al., 2008) it is over-expressed in high grade GBM and often co-expressed with HGF. Over-expression of c-Met in GBM reduces patient progression-free and overall survival times (Doo-Sik Kong et al., 2009).

Targeting c-Met c-Met is one of the most frequently genetically altered or otherwise dysregulated receptor tyrosine kinases in advanced human cancer and accordingly has been intensely investigated as a therapeutic target with several classes of agents being developed as novel therapeutics. These include small molecular weight tyrosine kinase inhibitors (TKI's), which prevent the activation of c-Met by acting as ATP-binding competitors for the TK domain. These TKI's have been shown to have anti-tumor activity in both in vitro and in vivo models (reviewed in Stellrecht et al., 2009, Eder J P et al., 2009, Comoglio P M et al., 2008; Tseng J R et al., (2008)), with several candidates currently being evaluated in clinical trials. Other approaches that have been used for targeting c-Met include the use of small interfering RNA (siRNA) and ribozymes which target c-met expression. RTK inhibitors include c-Met specific and more general tyrosine kinase inhibitors, including but not limited to K252a, SU11274 (Sugen). PH-665752 (Pfizer), ARQ197 (ArQule), XL880 (Exelesis), MP470 (SuperGen).

Another class of therapeutics are monoclonal antibodies (mAbs) directed to c-Met or HGF. The present inventors and others have shown that treatment of U87MG GBM xenografts with AMG 102, a fully human neutralizing antibody directed to HGF, significantly inhibits tumor growth (Burgess T et al., 2006, Pillay V et al., 2009). The agonist activity of anti-c-Met antibodies is often due to the antibody inducing receptor dimerisation and thus kinase activation.

DN30, described in Prat M et al., 1991, and Petrelli A et al., 2006 is a monoclonal antibody that binds to the beta chain of c-Met. The antibody behaves as a partial agonist since it induces phosphorylation of the receptor but does not activate the complete set of downstream biological effects of c-Met. The antibody has been found to cause c-Met receptor downregulation through a mechanism involving a double proteolytic cleavage. The c-Met downregulation effect appears to be dependent upon HGF (Petrelli A et al., 2006). The fact that this antibody causes initial activation of the c-Met receptor makes it problematic for therapy.

A further monoclonal MET4 has been described in Knudsen et al., 2009 and WO09/029591. This antibody recognizes an epitope on the alpha chain of human c-Met protein at amino acids 236-242. The antibody was developed as a diagnostic to recognize c-Met by immunohistochemistry in formalin fixed and paraffin embedded tissues. Neither of these disclosures mention anything as to whether this antibody exhibits any anti-tumor activity.

OA-5D5 is a one armed monoclonal anti-Met antibody comprising murine variable heavy and light chain domains and human IgG1 constant domains. This antibody has been described in Ohashi et al., 2000 and WO 06/015371 to Genentech. The OA-5D5 is derived from a fully agonistic anti-c-Met mAb and strongly inhibits the growth of HGF-dependent GBM xenografts in vivo but has no effect on HGF-independent GBM xenografts (Martens T et al., 2006).

More recently the creation of anti-c-Met Fab molecules R13 and R28 has been reported (van der horst E H et al., 2009). These Fab's act together through the initial binding of R13 locking c-Met into a conformation that stabilizes the R28 epitope. R28 then binds c-Met to block HGF binding.

Also, Pfizer CE-355621 antibody has shown efficacy in a U87 MG mouse xenograft model (Tseng et al (2008)).

As evidenced in the literature, there is clearly a strong interest in c-Met as a target for anti-tumor therapy and many different approaches are currently being explored. There is clearly a need for additional specific antibodies that successfully target c-Met on tumor cells in the absence of any receptor agonist activity, or that specifically inhibit c-Met activity, particularly TK activity.

The citation of references herein shall not be construed as an admission that such is prior art to the present invention.

SUMMARY OF THE INVENTION

In work leading up to the present invention, the inventors sought to produce antibodies capable of binding to c-Met for use as therapeutic and/or diagnostic reagents. A unique immunization strategy was used to generate the antibodies. This strategy involved immunizing mice with a purified fragment derived from human c-Met, containing amino acid residues 25-567 of c-Met as well as intact human c-Met over-expressing cells. The fragment contains an extra 3 amino acid residues (ETR) at the N-terminus and an extra 9 amino acids (ADL plus a terminal $His_6$ tag) at the C-terminus and corresponds to the sequence set forth in SEQ ID NO:1. The extra N and C-terminal amino acids allow for cloning of the c-Met fragment in frame with an Ig leader (N-terminus) and for purification (C terminal sequences).

Within the c-Met fragment used for the immunization protocol are located the N-terminal α-chain (amino acids 25-307) and the first 212 amino acids of the β chain (amino acids 308-519).

The sequence contains two domains, a 7-bladed beta-propeller and a small cysteine-rich domain (Gherardi et al., 2003). The beta propeller domain is now referred to as the "sema" domain proper. The beta propeller domain terminates at amino acid residue 514 of the c-Met sequence and the cysteine-rich domain encompasses amino acid residues 520-561 of c-Met. A short linker (amino acid residues 515 to 519) connects the two domains.

Using the unique approach of combining a physiologically relevant c-Met protein fragment (the fragment of SEQ ID NO:1) and A549 cells which constitutively over-express c-Met, the inventors identified a number of antibodies which were categorized into three subsets based on functional criteria. For example, the inventors identified various antibodies capable of binding to c-Met, one of which recognized an epitope of the beta chain of c-Met, six of which clearly recognized an epitope present on the alpha chain of c-Met, and three which appear to recognize a conformational eptiope. Such antibodies are important for therapeutic and/or diagnostic applications.

The antibodies identified herein represent compositions of matter capable of specifically binding to either the processed or unprocessed form of c-Met and modulating the function or activity of the c-Met receptor and, as a consequence, provide the basis for therapeutic and/or diagnostic reagents useful for characterizing and modulating c-Met and for treatment/detection of cancer. Furthermore, certain of the antibodies according to the invention are capable of inhibiting HGF-dependent and HGF-independent activation of the c-Met receptor.

The present invention provides an isolated antibody or antigen-binding fragment thereof that specifically binds to unprocessed c-Met present on the surface of a tumor cell.

Unprocessed c-Met is typically not found on the surface of normal cells. Thus, anti-c-Met antibodies capable of recognizing unprocessed c-Met are predicted to be tumor specific. The availability of c-Met tumor specific antibodies provides a means to identify and characterize tumors or cancer cells as being sensitive or susceptible to c-Met targeted therapies, including TK inhibitors, targeted siRNAs, and antibodies. The advantages of such tumor specific antibodies will be immediately recognizable to a person skilled in the art of the present invention.

The inventors have generated three antibodies, designed LMH 80, LMH 81 and LMH 82 which specifically recognise the unprocessed p170 form of c-Met at the cell surface. None of the epitopes recognized by these antibodies were found to overlap with the furin cleavage site (i.e. the site that separates the alpha and beta chains. Antibodies LMH 80/81 bind an alpha helical structure within the beta chain of c-Met while LMH 82 binds the loop connecting strands 2a and 2b on the bottom face of the MET beta-propeller domain. Using antibody LMH 80 and non-permeating immunofluorescence, the inventors were able to establish that the c-Met precursor is expressed on the cell surface of human cancer cells, in agreement with previous studies in human SkHep1 and LoVo cell lines (Gomes D A et al., (2008); Komada M et al (1993); Mondino A et al., (1991)). Additionally, there is evidence from murine derived cancer cells that the unprocessed p170 form of c-Met is exposed at the cell surface and can be activated by HGF (Rodrigues G A et al., (1991); Rong S et al., (1992)). Significantly, non-permeating analyses of primary non-cancerous rat hepatocytes suggested that p170 was unavailable for 125I-HGF binding at the cell surface (Mizuno, K et al., (1993)) strongly suggesting that p170 cell surface expression is specific for cancerous cells. The punctate c-Met staining described here for LMH 85 most likely represents non-covalent clusters of c-Met on the cell surface as reported previously (Faletto, D L et al., (1992)). As this pattern was also observed for LMH 80, it may indicate that p170 also forms similar non-covalent clusters on the cell surface. Thus antibodies LMH 80-82 may be useful for targeting radiotherapeutic and chemotherapeutic agents to tumors and protecting normal tissues such as liver from excessive levels of toxicity. Furthermore, as nanoparticle technology develops, these antibodies could be extremely useful tools for promoting the retention of such particles within the tumor mass.

In one example, the antibody or antigen-binding fragment thereof specifically binds to a sequence present on the alpha chain of unprocessed c-Met (p170). More particularly, the antibody or antigen-binding fragment thereof specifically binds to the epitope sequence VVDTYYDDQL (SEQ ID NO:2) on unprocessed c-Met. In another example, the antibody specifically binds to an epitope to which antibody LMH 82 deposited with the ATCC and produced by the hybridoma cell line designated PTA-11406 binds. In another example, the antibody is LMH 82 deposited with the ATCC and produced by the hybridoma cell line designated PTA-11406.

In another example, the antibody or antigen-binding fragment thereof comprises:
 (i) an immunoglobulin heavy chain comprising a variable region comprising an amino acid sequence substantially set out in each of, or one or more of the complementarity determining region (CDR) sequences SEQ ID NO:15, SEQ ID NO:16 and SEQ ID NO:17, and/or
 (ii) an immunoglobulin light chain comprising a variable region comprising an amino acid sequence substantially set out in each of, or one or more of the complementarity determining region (CDR) sequences SEQ ID NO:18, SEQ ID NO:19 and SEQ ID NO:20,
 wherein the antibody specifically binds c-Met.

In another example, the antibody or antigen-binding fragment thereof comprises:
 (i) an immunoglobulin heavy chain comprising a variable region amino acid sequence which is at least 90% identical to SEQ ID NO:21 and/or
 (ii) an immunoglobulin light chain comprising a variable region amino acid sequence which is at least 90% identical to SEQ ID NO:22.

In a preferred example, the immunoglobulin heavy chain comprises a variable region amino acid sequence at least 93%, 95%, 99% identical to SEQ ID NO:21. In a still further example, the immunoglobulin heavy chain comprises a variable region amino acid sequence set forth in SEQ ID NO:21.

In a preferred example, the immunoglobulin light chain comprises a variable region amino acid sequence at least 93%, 95%, 99% identical to SEQ ID NO:22. In a still further example, the immunoglobulin light chain comprises a variable region amino acid sequence set forth in SEQ ID NO:22.

In another example, the antibody or antigen-binding fragment thereof specifically binds to a sequence present on the beta chain of unprocessed c-Met (p170). In another example, the antibody or antigen-binding fragment thereof specifically binds to the epitope sequence RHFQSCSQCLSAP-PFVQCGW (SEQ ID NO:5) or to the epitope sequence RHFQSCSQCLSAPPF (SEQ ID NO:6) on unprocessed c-Met. In another example, the antibody specifically binds to an epitope to which antibody LMH-80 deposited with the ATCC and produced by the hybridoma cell line designated PTA-11405 binds. In another example, the antibody is LMH 80 deposited with the ATCC and produced by the hybridoma cell line designated PTA-11405.

In another example, the antibody or antigen-binding fragment thereof comprises:
 (i) an immunoglobulin heavy chain comprising a variable region comprising an amino acid sequence substantially set out in each of, or one or more of the complementarity determining region (CDR) sequences SEQ ID NO:7, SEQ ID NO:8 and SEQ ID NO:9, and/or
 (ii) an immunoglobulin light chain comprising a variable region comprising an amino acid sequence substantially set out in each of, or one or more of the complementarity determining region (CDR) sequences SEQ ID NO:10, SEQ ID NO:11 and SEQ ID NO:12,
 wherein the antibody specifically binds c-Met.

In another example, the antibody or antigen-binding fragment thereof comprises:
(i) an immunoglobulin heavy chain comprising a variable region amino acid sequence which is at least 90% identical to SEQ ID NO:13 and/or
(ii) an immunoglobulin light chain comprising a variable region amino acid sequence which is at least 90% identical to SEQ ID NO:14.

In a preferred example, the immunoglobulin heavy chain comprises a variable region amino acid sequence at least 93%, 95%, 99% identical to SEQ ID NO:13. In a still further example, the immunoglobulin heavy chain comprises a variable region amino acid sequence set forth in SEQ ID NO:13.

In a preferred example, the immunoglobulin light chain comprises a variable region amino acid sequence at least 93%, 95%, 99% identical to SEQ ID NO:14. In a still further example, the immunoglobulin light chain comprises a variable region amino acid sequence set forth in SEQ ID NO:14.

The inventors have surprisingly found that certain of the anti-c-Met antibodies of the invention are able to induce downregulation of the c-Met receptor without causing receptor autoactivation. Antibodies of the prior art typically cause receptor activation and hence function as agonist or otherwise behave as partial agonists by initially activating the receptor prior to downregulation. Anecdotally, it has been found that antibodies which induce autoactivation of the c-Met receptor can lead to retinal problems. Moreover, the antibodies of the invention were found to inhibit ligand and non-ligand dependent activation of the c-Met receptor. Accordingly, antibodies which are able to induce c-Met receptor downregulation in the absence of any initial autoactivation are particularly advantageous for cancer therapy, including the possibility of enhanced efficacy in the absence of significant side effects or toxicity. For example, this allows for greater concentrations of the antibody to be used without risk of toxicity and with fewer side effects. The ability to design a therapeutic agent which exhibits fewer side effects compared with the standard therapy provides a clinician with a particularly effective and desirable agent.

Accordingly, the invention also provides an isolated antibody or antigen-binding fragment thereof that specifically binds to c-Met on a tumor cell and induces downregulation of receptor in the absence of c-Met receptor activation. In particular, the antibody or antigen-binding fragment thereof induces c-Met receptor downregulation regardless of receptor autoactivation or the presence of the HGF ligand.

In one example, the antibody or antigen-binding fragment thereof specifically binds to a c-Met alpha chain epitope sequence consisting of the core sequence DVLPEFRDSY (SEQ ID NO:4).

In yet a further example, the antibody or antigen-binding fragment thereof comprises an immunoglobulin heavy chain comprising a variable region amino acid sequence set forth in SEQ ID NO:29 and/or an immunoglobulin light chain comprising a variable region amino acid sequence set forth in SEQ ID NO:30.

In another example, the invention provides an antibody or antigen-binding fragment thereof which induces c-Met receptor downregulation in the absence of receptor activation, the antibody comprising an immunoglobulin heavy chain comprising a variable region amino acid sequence set forth in SEQ ID NO:29 and/or an immunoglobulin light chain comprising a variable region amino acid sequence set forth in SEQ ID NO:30.

A person skilled in the art of the invention will be capable of determining whether a given antibody or antigen-binding fragment thereof is capable of inducing c-Met receptor downregulation/degradation. Such assays include those described in the specification herein in the Examples.

The invention also provides an isolated antibody or antigen-binding fragment thereof which comprises:
i) an immunoglobulin heavy chain comprising a variable region amino acid sequence which is at least 90% identical to SEQ ID NO:29 and/or
ii) an immunoglobulin light chain comprising a variable region amino acid sequence which is at least 90% identical to SEQ ID NO:30,
wherein the antibody specifically binds c-Met.

Preferably, the antibody or antigen-binding fragment thereof induces downregulation of the c-Met receptor in the absence of receptor activation.

In a preferred example, the immunoglobulin heavy chain comprises a variable region amino acid sequence at least 93%, 95%, 99% identical to SEQ ID NO:29. In a still further example, the immunoglobulin heavy chain comprises a variable region amino acid sequence set forth in SEQ ID NO:29.

In a preferred example, the immunoglobulin light chain comprises a variable region amino acid sequence at least 93%, 95%, 99% identical to SEQ ID NO:30. In a still further example, the immunoglobulin light chain comprises a variable region amino acid sequence set forth in SEQ ID NO:30.

The invention also provides an isolated antibody or antigen-binding fragment thereof which comprises:
(i) an immunoglobulin heavy chain comprising a variable region comprising an amino acid sequence substantially set out in each of, or one or more of the complementarity determining region (CDR) sequences SEQ ID NO:23, SEQ ID NO:24 and SEQ ID NO:25 and/or
ii) an immunoglobulin light chain comprising a variable region comprising an amino acid sequence substantially set out in each of, or one or more of the complementarity determining region (CDR) sequences SEQ ID NO:26, SEQ ID NO:27 and SEQ ID NO:28
wherein the antibody specifically binds c-Met.

Preferably, the antibody or antigen-binding fragment thereof induces downregulation of the c-Met receptor in the absence of receptor activation.

In another example, the antigen-binding fragment according to the above is an scFV comprising:
i) an immunoglobulin heavy chain comprising a variable region amino acid sequence of SEQ ID NO:29 and/or
ii) an immunoglobulin light chain comprising a variable region amino acid sequence of SEQ ID NO:30.

It will be appreciated by persons skilled in the art of the present invention that downregulation of the c-Met receptor on a tumor cell results in the inhibition of cellular proliferation and invasion and the induction of apoptosis.

Accordingly, the invention also provides a method of inhibiting cellular proliferation of a tumor cell in a subject, comprising administering to the subject, an antibody or antigen binding fragment thereof according to the invention that induces c-Met receptor downregulation in the absence of receptor activation. In one example, the antibody is LMH 87 comprising an immunoglobulin heavy chain comprising a variable region amino acid sequence comprising SEQ ID NO:29 and/or an immunoglobulin light chain comprising a variable region amino acid sequence comprising SEQ ID NO:30.

In another example, the method of inhibiting cellular proliferation of a tumor cell in a subject, comprising administering to the subject an isolated antibody or antigen-binding fragment thereof, the antibody comprising:
(i) an immunoglobulin heavy chain comprising a variable region comprising an amino acid sequence substantially set out in each of, or one or more of the complementarity determining region (CDR) sequences SEQ ID NO:23, SEQ ID NO:24 and SEQ ID NO:25 and/or ii) an immunoglobulin light chain comprising a variable region comprising an amino acid sequence substantially set out in each of, or one or more of the complementarity determining region (CDR) sequences SEQ ID NO:26, SEQ ID NO:27 and SEQ ID NO:28.

Preferably, the antibody or antigen-binding fragment thereof inhibits cellular proliferation by inducing c-Met receptor downregulation/degradation.

In another example, the method of inhibiting tumor cell proliferation by inducing c-Met receptor downregulation/degradation is achieved by administrating to the subject an scFv based on antibody LMH 87.

In another example, the method of inhibiting tumor cell proliferation by inducing c-Met receptor downregulation/degradation is achieved by administrating to the subject antibody LMH 88 which binds to the same epitope sequence as LMH 87.

The antibody or antigen-binding fragment thereof may be administered together with one or more other therapeutics. Examples of suitable other therapeutics include agents that target the epidermal growth factor (EGF) receptor, agents that target senescence-associated receptor-like kinase (SARK) or anti-angiogenesis agents.

The invention also provides an isolated antibody or antigen-binding fragment thereof that specifically binds to an epitope present on an alpha or beta chain of c-Met, the epitope comprising or consisting essentially of an amino acid sequence selected from the group consisting of WDTYYDDQL (SEQ ID NO:2), VRRLKETKDGFMFLT (SEQ ID NO:3), DVLPEFRDSY (SEQ ID NO:4), and RHFQSCSQCLSAPPF (SEQ ID NO:6).

In one example, the antibody or antigen-binding fragment thereof specifically binds to the c-Met epitope sequence RHFQSCSQCLSAPPFVQCGW (SEQ ID NO:5). In another example, the antibody binds to a core epitope sequence consisting of the sequence DVLPEFRDSY (SEQ ID NO:4).

In another example, the antibody or antigen-binding fragment thereof specifically binds to the core epitope sequence VRRLKETKDGFMFLT (SEQ ID NO:3). In another example, the antibody specifically binds to the epitope sequence VRRLKETKDGFMFLT (SEQ ID NO:3) to which antibody LMH 84 binds.

The antibodies according to the invention bind to the c-Met receptor with varying degrees of affinity. In one example, the invention provides an antibody or antigen-binding fragment thereof that specifically binds to the c-Met epitope comprising the sequence RHFQSCSQCLSAPPFVQCGW (SEQ ID NO:5) with an affinity in the range of about 10-35 nM. In another example, the invention provides an antibody or antigen-binding fragment thereof that specifically binds to the c-Met epitope comprising the sequence DVLPEFRDSY (SEQ ID NO:4) with low affinity, preferably an affinity less than 5 nM, more particularly about 3 nM. In one particular example, the invention provides an antibody, designated LMH 87 which binds to the epitope sequence DVLPEFRDSY (SEQ ID NO:4) and comprises heavy and light chain variable region sequences set forth in SEQ ID NO:29 and SEQ ID NO:30 respectively. In another example, the invention provides an antibody or antigen-binding fragment thereof that specifically binds to the c-Met epitope comprising the sequence DVLPEFRDSY (SEQ ID NO:4) with high affinity, preferably an affinity greater than 70 nM, more particularly about 75 nM. Methods for assaying antigen-binding affinity are well known in the art and include half-maximal binding assays, competition assays, BIAcore and Scatchard analysis.

In another example, the invention provides an isolated antibody or antigen-binding fragment thereof that specifically binds to an epitope of c-Met consisting of the core epitope sequence DVLPEFRDSY (SEQ ID NO:4), wherein the antibody is not a Met4 antibody produced by the hybridoma cell line deposited with the ATCC under Accession No. PTA-7680.

The invention also provides an antibody or antigen-binding fragment thereof which is capable of competitively inhibiting binding of an antibody of the invention to an epitope selected from the group consisting of VVDTYYDDQL (SEQ ID NO:2), VRRLKETKDGFMFLT (SEQ ID NO:3), DVLPEFRDSY (SEQ ID NO:4), RHFQSCSQCLSAPPFVQCGW (SEQ ID NO:5) and RHFQSCSQCLSAPPF (SEQ ID NO:6).

The invention also provides an antibody to antigen-binding fragment thereof which is capable of competitively inhibiting an antibody of the invention as described herein, for example an antibody designated LMH 80, LMH 82, LMH 84, LMH 85, or LMH 87.

The invention also provides an antibody which is an agonist of the c-Met receptor. In one example, the invention provides an agonist anti-c-Met antibody LMH 85 comprising:

i) an immunoglobulin heavy chain comprising a variable region comprising an amino acid sequence which is at least 90% identical to SEQ ID NO:37 and/or ii) an immunoglobulin light chain comprising a variable region comprising an amino acid sequence which is at least 90% identical to SEQ ID NO:38 wherein the antibody specifically binds c-Met.

In a preferred example, the immunoglobulin heavy chain comprises a variable region amino acid sequence at least 93%, 95%, 99% identical to SEQ ID NO:37. In a still further example, the immunoglobulin heavy chain comprises a variable region amino acid sequence set forth in SEQ ID NO:37.

In a preferred example, the immunoglobulin light chain comprises a variable region amino acid sequence at least 93%, 95%, 99% identical to SEQ ID NO:38. In a still further example, the immunoglobulin light chain comprises a variable region amino acid sequence set forth in SEQ ID NO:38.

In another example, the present invention also provides an agonist anti-c-Met antibody LMH 85 comprising:

i) an immunoglobulin heavy chain comprising a variable region comprising an amino acid sequence substantially set out in each of, or one or more of the complementarity determining regions (CDRs) set forth in SEQ ID NO:31, SEQ ID NO:32 and SEQ ID NO:33 and/or ii) an immunoglobulin light chain comprising a variable region comprising an amino acid sequence substantially set out in each of, or one or more of the complementarity determining regions (CDRs) set forth in SEQ ID NO:34, SEQ ID NO:35 and SEQ ID NO:36 wherein the antibody specifically binds c-Met.

Surprisingly, the inventors have found that an scFv based on LMH 85 exhibited antagonist activity by blocking HGF activation of c-Met. Accordingly, the invention also provides an scFv comprising an immunoglobulin heavy chain comprising a variable region sequence of SEQ ID NO:37 and an immunoglobulin light chain comprising a variable region sequence of SEQ ID NO:38.

The invention also provides any of the antibodies or antigen binding fragments thereof or scFv according to the invention conjugated to an agent, preferably a detectable or functional label or a therapeutic agent. Particularly preferred antibodies are those that specifically bind to the unprocessed form of c-Met as exemplified by antibodies LMH 80, LMH 81 or LMH 82.

The therapeutic agent can be directly or indirectly bound to the antibody. Examples of therapeutic agents include, but are not limited to, a cytotoxin, a radioisotope (for instance, iodine-131, yttrium-90 or indium-111), an immunomodulatory agent, an anti-angiogenic agent, an anti-neovascularization and/or other vascularization agent, a toxin, an anti-proliferative agent, a pro-apoptotic agent, a chemotherapeutic agent, tyrosine kinase inhibitor and a therapeutic nucleic acid.

The antibody according to the invention may be a polyclonal or monoclonal antibody. The antibody or antigen-binding fragment thereof may be a chimeric antibody, a humanised antibody, or a human antibody. Alternatively, the antibody may be produced by recombinant means. Preferably, the antibodies or antigen-binding fragments described herein comprise human variable region framework sequences and constant region sequences.

The antibodies of the invention can belong to any antibody class, IgM, IgG, IgE, IgA, IgD, or subclass. Exemplary subclasses for IgG are $IgG_1$, $IgG_2$, $IgG_3$ and $IgG_4$.

The antigen-binding fragment according to the invention may be selected from Fab, Fab', $F(ab')_2$, Fv, Fd, single-chain Fv (scFv), disulfide-linked Fvs (sdFv), $V_L$ and $V_H$ domain fragments, domain antibody, trispecific ($Fab_3$), bispecific ($Fab_2$), diabody (($V_L$-$V_H$)$_2$ or ($V_H$-$V_L$)$_2$), triabody (trivalent), tetrabody (tetravalent), minibody ((scFv-$CH_3$)$_2$), bispecific single-chain Fv (Bis-scFv), IgGdeltaCH2, scFv-Fc and $(scFv)_2$-Fc.

The present invention also provides an isolated nucleic acid sequence encoding an antibody or antigen-binding fragment described herein according to any example. Accordingly, the invention also extends to the nucleotide acid sequences of the antibodies described herein. Accordingly, in one example, the antibody or antigen-binding fragment comprises an immunoglobulin heavy chain variable region comprising the nucleic acid sequence of SEQ ID NO:39 and/or an immunoglobulin light chain variable region comprising the nucleic acid sequence of SEQ ID NO:40. In another example, the antigen-binding fragment is an scFv comprising or consisting of an immunoglobulin heavy chain variable region comprising the nucleic acid sequence of SEQ ID NO:41 and/or an immunoglobulin light chain variable region comprising the nucleic acid sequence of SEQ ID NO:42.

The present invention also provides a vector comprising one or more nucleic acid sequences of the invention. In one example, the vector comprises a nucleic acid sequence encoding an antibody or antigen-binding fragment as set forth herein. In one example, the vector comprises a nucleic acid sequence comprising a heavy chain variable region comprising the sequence of SEQ ID NO:39 and/or a light chain variable region sequence comprising the sequence of SEQ ID NO:40. In another example, the vector comprises a nucleic acid sequence comprising a heavy chain variable region comprising the sequence of SEQ ID NO:41 and/or a light chain variable region comprising the sequence of SEQ ID NO:42. In a further example, the vector comprises a heavy chain variable region nucleic acid sequence encoding the sequence of SEQ ID NO:13 and/or a light chain variable region nucleic acid sequence encoding the sequence of SEQ ID NO:14. In a further example, the vector comprises a heavy chain variable region nucleic acid sequence encoding the sequence of SEQ ID NO:21 and/or a light chain variable region nucleic acid sequence encoding the sequence of SEQ ID NO:22.

The invention also provides a transformed or transfected host cell comprising a nucleic acid sequence of the invention that expresses an antibody or antigen-binding fragment thereof according to the invention. The host cell preferably comprises the vector according to the invention. The host cell can be any cell type such as a bacterial, yeast, plant or animal cell.

The present invention also provides a process for producing an anti-c-Met antibody of the invention comprising culturing a host cell of the invention so that the nucleic acid is expressed and the antibody produced, wherein the host cell comprises at least one nucleic acid sequence of the invention. In one example, the immunoglobulin light chain and the immunoglobulin heavy chain are encoded by two separate open reading frames on one contiguous nucleic acid.

The invention also provides a pharmaceutical composition comprising the antibody or antigen-binding fragment thereof, scFv or antibody conjugate according to the invention together with a pharmaceutically acceptable carrier or excipient. In one example, the composition comprises an antibody or antigen-binding fragment thereof comprising an immunoglobulin heavy chain variable region comprising an amino acid sequence of SEQ ID NO:13, or SEQ ID NO:21, or SEQ ID NO:29, or SEQ ID NO:37 and/or an immunoglobulin light chain comprising a variable region comprising an amino acid sequence of SEQ ID NO:14, SEQ ID NO:22, SEQ ID NO:30 or SEQ ID NO:38, together with a pharmaceutically acceptable carrier or excipient. In another example, the composition comprises an antibody produced by a hybridoma according to the invention (designated PTA-11405 or PTA-11406), together with a pharmaceutically acceptable carrier or excipient.

The composition of the present invention may be administered alone or in combination with other treatments, therapeutics or agents, either simultaneously or sequentially depending upon the condition to be treated. The present invention contemplates or includes compositions comprising the antibody or antigen-binding fragment of the invention herein described and other agents or therapeutics such as anti-cancer agents or therapeutics, inhibitors of angiogenesis or immune modulators. The anti cancer agents or therapeutics may be one or more anti-cancer antibody or active fragment(s) thereof. The antibody(ies) may be specific for a tumor antigen or protein or receptor which is altered or overexpressed in cancer cells or tumors. In an exemplary such embodiment the anti-cancer agent may be an anti-EGFR agent or antibody (such as those described in WO 02/092771, WO 05/081854 and WO 09/023265). More generally, the anti-cancer agents may be tyrosine kinase inhibitors or phosphorylation cascade inhibitors, post-translational modulators, cell growth or division inhibitors and signal transduction inhibitors. Typical anti-cancer agents according to the invention include anti-neoplastic agents, for example, doxorubicin, carboplatin, temozolomide and cisplatin. Typical immune modulators according to the invention include interleukins, tumor necrosis factor (TNF) and other growth factors, cytokines, or hormones such as dexamethasone which stimulate the immune response and reduce or eliminate cancer cells or tumors.

The antibody, antigen-binding fragment thereof or conjugate according to the invention may be used in a method of treatment or diagnosis or the human or animal body, such as a method of treating undesirable cell proliferation or a cell proliferative disorder in a subject which comprises administering to said subject a therapeutically effective amount of an antibody or antigen-binding fragment thereof, scFv or antibody conjugate according to the invention. Preferably, the method is used to treat cancer.

In one example, the present invention provides a method for diagnosing a disorder in a subject, the method comprising contacting the subject, or a sample obtained therefrom, with an antibody, antibody fragment or antibody conjugate of the invention and analysing the subject or sample for binding between human c-Met and the antibody or antibody conjugate. The method can be performed in vitro or in vivo. The invention thus provides a method for diagnosing or monitoring cancer or a cancerous condition, particularly a c-Met mediated cancer or tumor.

In an example, the method is performed in vitro using histological specimens or subfractions of tissue or fluid obtained from the subject. In an additional example, the method is performed in vivo or ex vivo using cultured tumor biopsy or sample cells using labelled antibody and any available and suitable imaging or assessment methods.

The present invention also provides a method of detecting the presence or absence or amount of human c-Met in a sample, the method comprising contacting the sample with an antibody, antibody fragment of the invention, or a conjugate of the invention, and analysing the sample for binding between human c-Met and the antibody or conjugate.

Examples of suitable samples which can be tested include, but are not necessarily limited to, blood, serum, plasma, as well as cell, tumor or tissue biopsies.

The present invention also provides for use of an antibody or antigen-binding fragment thereof according to the invention in assays to characterise tumors or cellular samples or to screen for tumors or cancer, including in vitro, ex vivo and in vivo diagnostic assays, or for the manufacture of a reagent for diagnosing a cell proliferative disorder manifested by c-Met in a subject.

The invention provides an assay system for screening potential drugs effective to modulate the presence or activity of c-Met and/or the activity or binding of the antibody of the present invention. The antigen peptide or antibody may be introduced into a test system, and the prospective drug may also be introduced into the resulting cell culture, and the culture thereafter examined to observe any changes in the activity of the cells, binding of the antibody, or amount and extent HGF-responsive activity due either to the addition of the prospective drug alone, or due to the effect of added quantities of the known agent(s).

The present invention also provides for use of an antibody or antigen-binding fragment, or antibody conjugate thereof according to the invention in medicine. For example, the present invention also provides for the use of an antibody or antigen-binding fragment thereof or antibody conjugate according to the invention in the manufacture of a medicament for reducing undesirable cell proliferation or modulating or treating a cell proliferative disorder in a subject. Preferably, the medicament is used to treat cancer.

The present invention also provides for the use of an antibody conjugate of the invention for anti-tumor therapy in a subject. It will be appreciated that such conjugates can be used to deliver a therapeutic agent or imaging agent according to the invention.

The invention also provides a method of inhibiting undesirable cell proliferation in a subject, comprising administering to a subject an antibody or antigen-binding fragment according to the invention or antibody conjugate according to the invention. In one example, the method is practised with an antibody or antigen-binding fragment thereof comprising a immunoglobulin heavy chain variable region sequence comprising SEQ ID NO:13, SEQ ID NO:21, SEQ ID NO:29 or SEQ ID NO:37 and/or an immunoglobulin light chain variable region sequence comprising SEQ ID No:14, SEQ ID NO:22, SEQ ID NO:30 or SEQ ID NO:38.

Preferably, the method is used to treat cancer.

In another example, the method is practised with an scFv comprising an immunoglobulin heavy chain variable region sequence comprising SEQ ID NO:37 and an immunoglobulin light chain variable region sequence comprising SEQ ID NO:38.

The invention also provides an vaccine antigen comprising or consisting of the sequence RHFQSCSQCLSAP-PFVQCGW (SEQ ID NO:5) or RHFQSCSQCLSAPPF (SEQ ID NO:6), together with a pharmaceutically acceptable carrier or excipient. In a preferred embodiment, the vaccine is used to treat cancer.

The invention also provides a method of immunizing an animal to obtain an anti-c-Met antibody, comprising administering to the animal a truncated c-Met antigen fragment comprising the sequence of SEQ ID NO:1, in sequence with or together with cells over-expressing c-Met. In one example, the antigen fragment and cells are administered to the animal on an alternating basis. The animal according to this example is preferably a mouse, rat or rabbit.

In another example, the animal is immunized with an antigen peptide sequence comprising a sequence selected from the group consisting of VVDTYYDDQL (SEQ ID NO:2), VRRLKETKDGFMFLT (SEQ ID NO:3), DVLPEFRDSY (SEQ ID NO:4), and RHFQSCSQCLSAPPFVQCGW (SEQ ID NO:5).

The invention also provides an antibody or antigen-binding fragment thereof produced by the immunization method according to the invention.

It has been found that c-Met amplification leads to gefitinib resistance in lung cancer cells by activating ERBB3 signaling (Engelman J A et al., 2007). Accordingly, the present invention also provides for the use of an antibody or antigen-binding fragment according to the invention to overcome or alleviate resistance to a chemotherapeutic agent in a cancer cell. In a preferred example, the antibody or antigen-binding fragment thereof according to the invention is capable of overcoming resistance to treatment with a chemotherapeutic agent, wherein the resistance is caused by amplification of c-Met. Chemotherapeutic agents are known to persons skilled in the art and include such agents described elsewhere in this document.

In one example, the antibody or antigen-binding fragment is the LMH 87 antibody comprising an immunoglobulin heavy chain comprising a variable region amino acid sequence comprising SEQ ID NO:29 and/or an immunoglobulin light chain comprising a variable region amino acid sequence comprising SEQ ID NO:30.

In another example, the antibody is an scFv (scFv 85) comprising an immunoglobulin heavy chain comprising a variable region amino acid sequence comprising SEQ ID NO:37 and/or an immunoglobulin light chain comprising a variable region amino acid sequence comprising SEQ ID NO:38.

or antibodies LMH 80, 84 and 87. 25H2 recognizes the unprocessed form of c-Met (containing both α and β-chain) and the c-Met β-chain. (C) Immunoprecipitation of selected LMH antibodies. c-Met was immunoprecipitated from A549 cell lysates using 5 µg/ml of antibody (LMH 85, 86, 87, 88 and 89). Subsequently the immunoprecipitated c-Met was blotted with mAb 25H2, a commercial antibody. (D) Immunoblots showing agonist/antagonist activity of selected LMH antibodies. A459 cells were treated with either antibody alone or antibody in the presence of HGF ligand and whole cell lysates prepared. Samples were probed for total c-Met (upper panels) or phosphorylated c-Met (Y1234/Y1235) (lower panels). (E) Effect of selected LMH antibodies on cell migration. Antibodies were tested for their ability to induce cell migration in SK-OV-3 cells. Antibody LMH 85 stimulated cell migration with antibody LMH 87 had no effect (upper panel). Differing concentrations of LMH 87 were mixed with 300 pM HGF to determine if it inhibited the HGF induced migration of SK-OV-3 cells. Antibody LMH 87 partially inhibited the migratory activity stimulated by HGF (lower panel). Data in both graphs are presented as percentage migration versus 300 pM HGF±SD.

Figure 2:
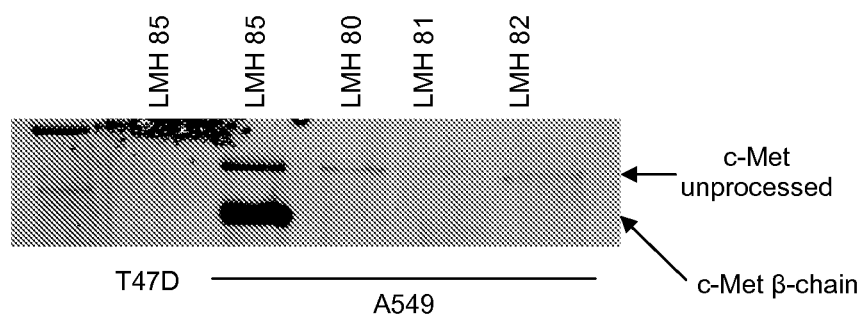

FIG. 2 The c-met from A549 cells was immunoprecipitated by antibodies LMH 80, 81, 82 or 85, and western blotted with 25H2 that recognizes the beta-chain of c-Met in both the unprocessed and processed forms of the receptor. Identical samples were run in duplicate.

Figure 3:
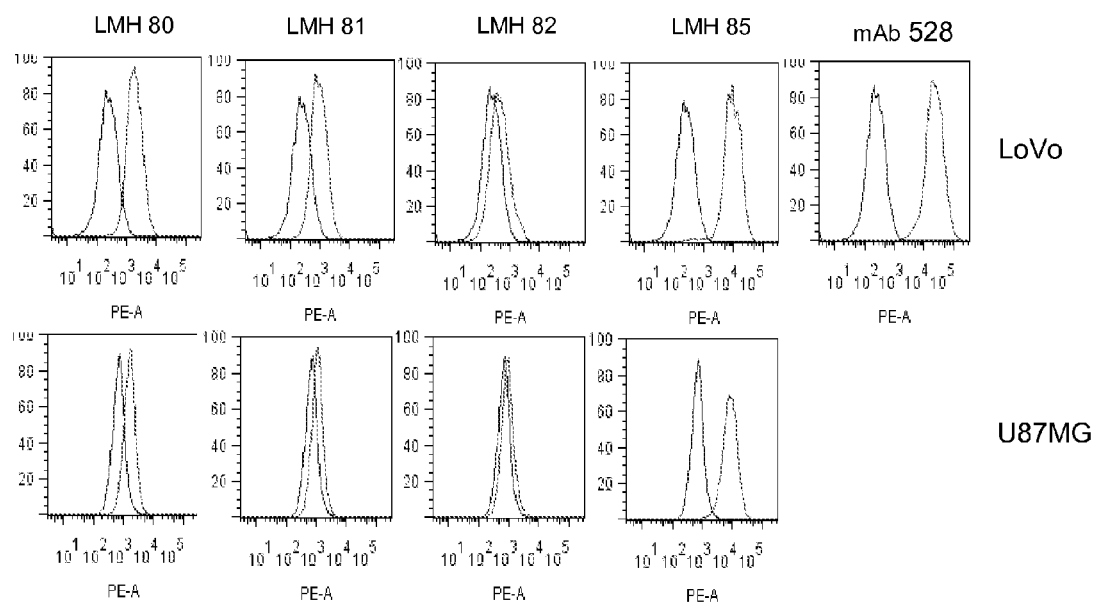

FIG. 3 Flow cytometry analysis of binding of LMH antibodies 80, 81 or 82 and antibody 85 to c-Met on LoVo colon cancer cells (upper panel) which predominantly express unprocessed c-Met and U87MG cells (lower panel). Binding was detected using phycoerythrin (PE) labelled anti-mouse secondary antibodies. mAb 528, which binds the EGFR, was used as a positive control. Negative controls were non-specific isotype-matched primary antibody followed by secondary antibody. These are represented by the histogram on the left.

Figure 4:
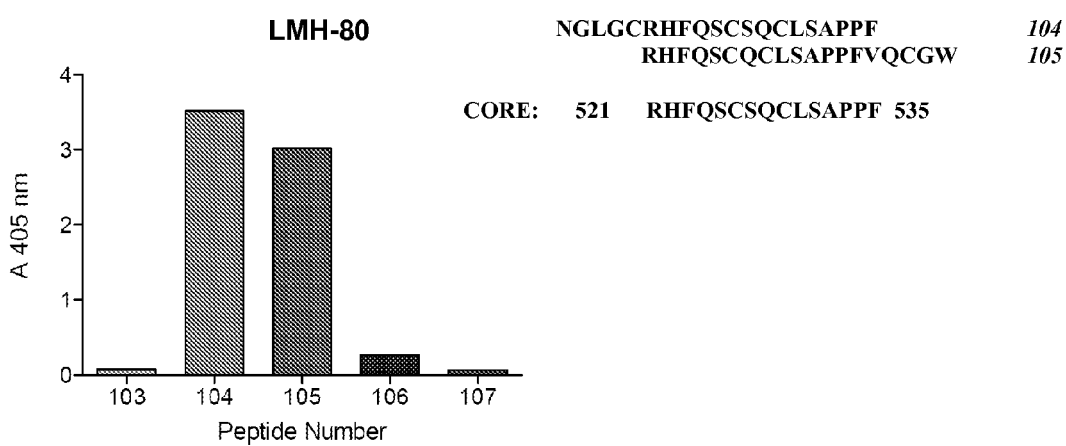
Figure 4:
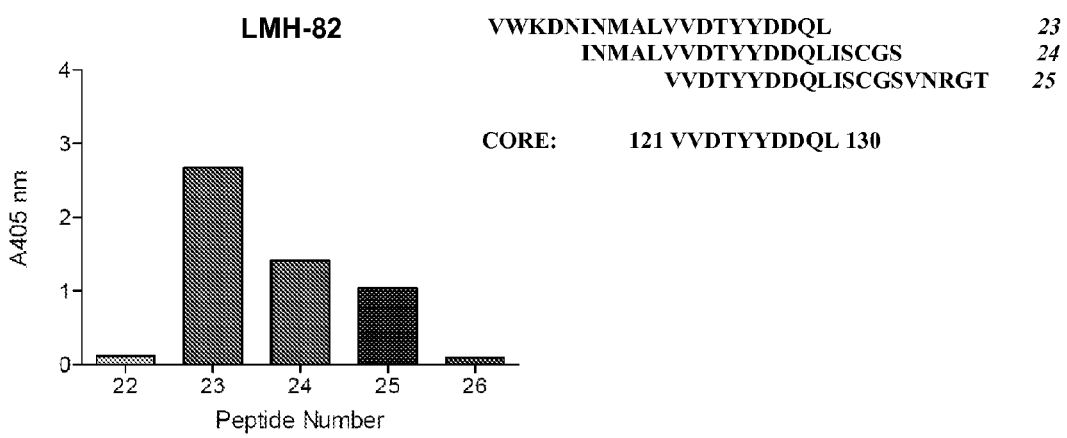
Figure 4:
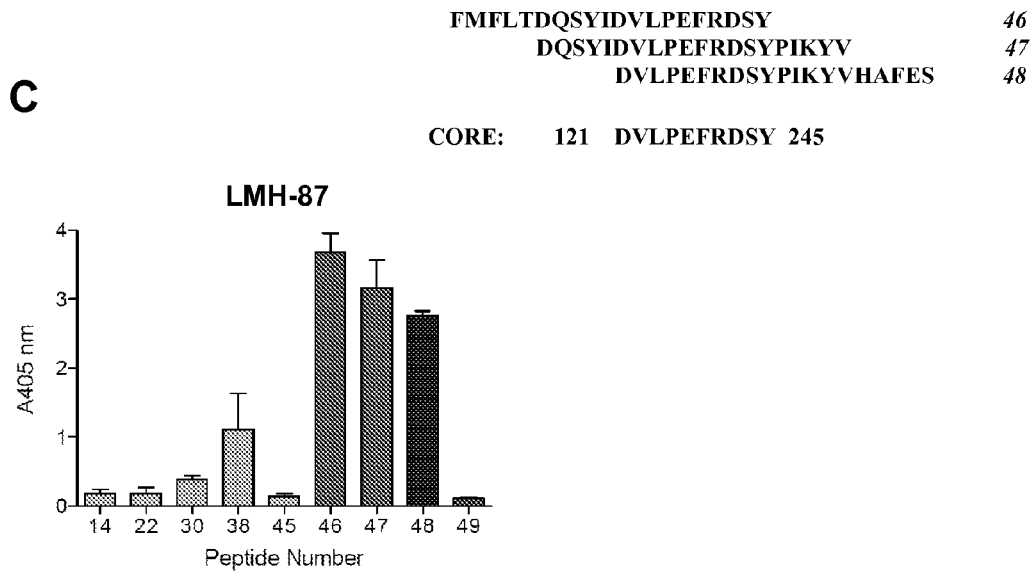

FIG. 4 Epitope mapping of the LMH antibodies. Antibodies were tested against a panel of overlapping biotinylated peptides representing the entire c-Met SEMA domain. An antibody's reactivity was determined by standard ELISA and the results were graphed, with data showing the mean absorbance reading for selected peptides±SEM. The data for (A) antibody LMH 80, (B) antibody LMH 82, (C) LMH 87 antibodies are shown. The peptide sequences bound by the antibody were aligned (right of each graph) to determine the core epitope. In (A) LMH-80 bound peptides peptide 104 NGLGCRHFQSCSQCLSAPPF (SEQ ID NO:44), peptide 105 RHFQSCSQLSAPPFVQCGW (SEQ ID NO:5) and core sequence RHFQSCSQCLSAPPF (SEQ ID NO:6) are indicated. In (B) LMH-82 bound peptides peptide 23 VVKDNINMALVVDTYYDDQL (SEQ ID NO:45), peptide 24 INMALVVDTYYDDQLISCGS (SEQ ID NO:46), peptide 25 VVDTYYDDQLISCGSVNRGT (SEQ ID NO:47) and core sequence VVDTYYDDQL (SEQ ID NO:2) are indicated. In (C) LMH-87 bound peptides peptide 46 FMFLTDQSYIDVLPEFRDSY (SEQ ID NO:48), peptide 47 DQSYIDVLPEFRDSYPIKYV (SEQ ID NO:49), peptide 48 DVLPEFRDSYPIKYVHAFES (SEQ ID NO: 50) and core sequence DVLPEFRDSY (SEQ ID NO:4) are indicated.

Figure 5:
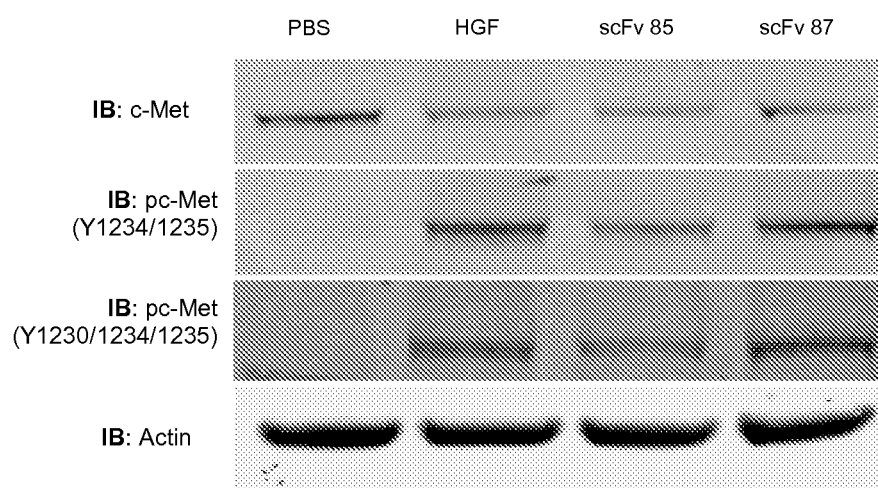

FIG. 5 Antagonist activity of single chain (scFv) variable fragment of antibody LMH 85. Whole cell lysates of A549 cells treated with either scFv 85 or scFv 87 and HGS were probed for either total c-Met, phosphorylated c-Met (Tyr1234/1235) and (Tyr1230/1234/1235) or a pan-actin antibody to control for loading.

Figure 6:
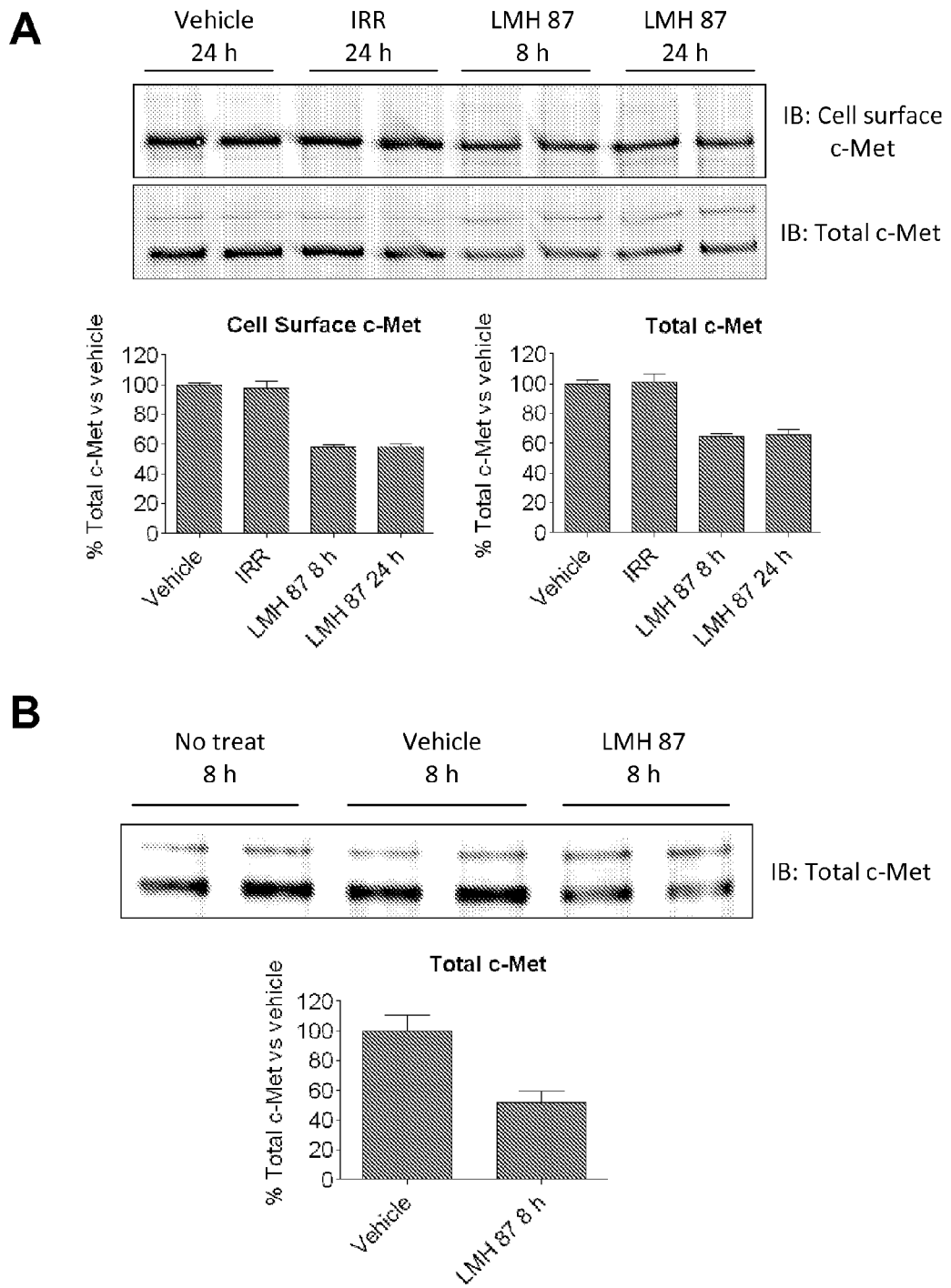

FIG. 6 LMH 87 down-regulates total surface c-Met and inhibits tumor cell growth. (A) c-Met was immunoprecipitated from A549 lung cancer cells that had been treated with antibody LMH 87 and then cell surface biotinylated. Cell surface c-Met (upper blot) and total c-Met (lower blot) remaining following incubation with LMH 87. Bar graphs show quantification by densitometry. (B) Total c-Met remaining in U87MG glioma cells following incubation with LMH 87. Bar graphs show quantification by densitometry. Both (A) and (B) are representative blots of repeated experiments.

Figure 7:
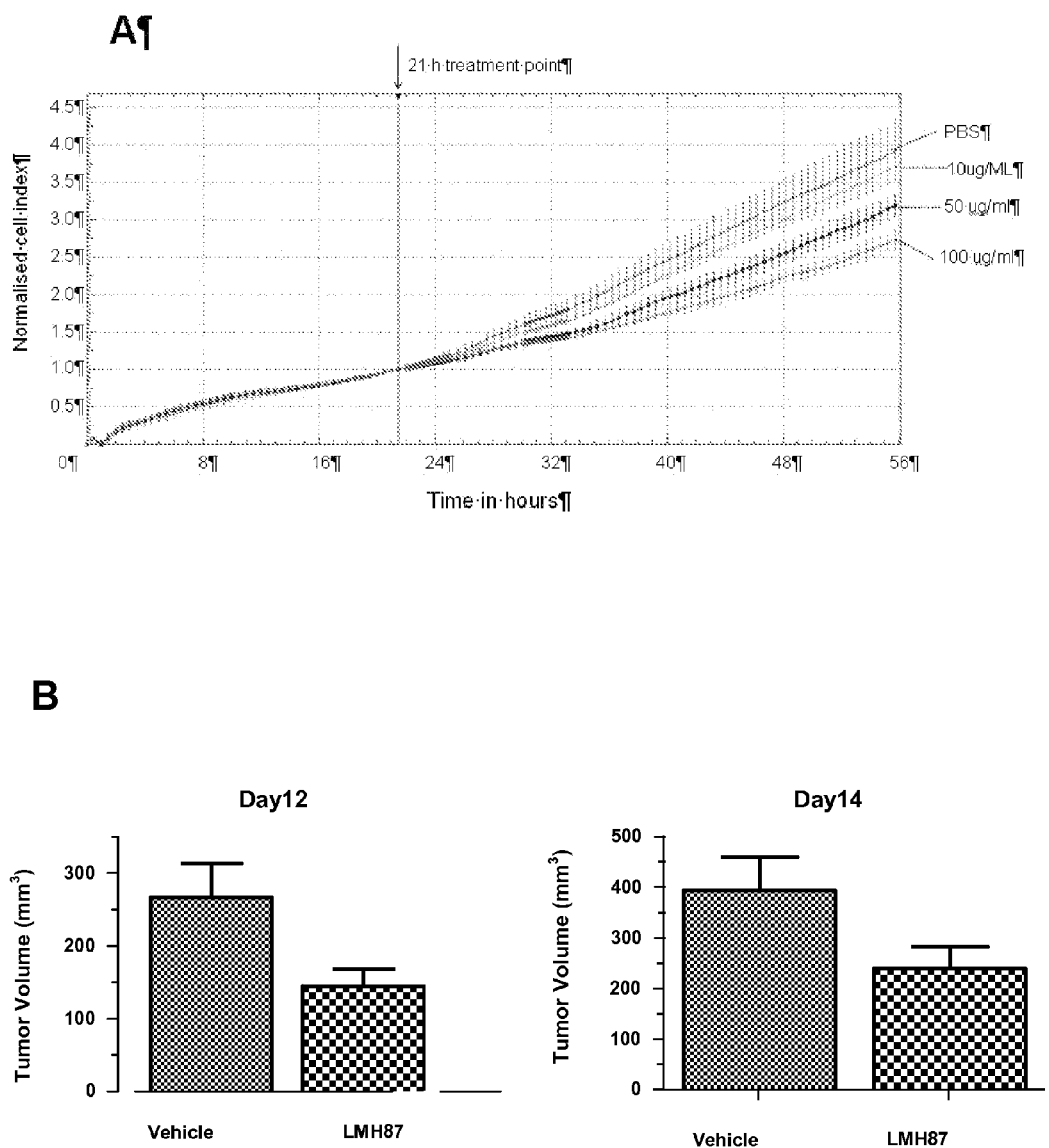

FIG. 7 LMH 87 inhibition of tumor cell growth in vitro and in vivo. (A) xCelligence analysis on A549 cells treated with LMH 87. A549 cells were treated with either PBS or multiple doses of LMH 87; 10 µg/ml, 50 µg/ml, and 100 µg/ml. Data is presented as the cell index normalised to 21 h±SEM, the time point when the antibody was added. (B) U87MG xenografts treated with LMH 87. Mice were implanted with U87MG cells and injected three times (days 7, 10 and 12) with 1 mg of LMH 87 or vehicle. Data is presented as the mean tumor size in $mm^3$±SEM.

KEY TO SEQUENCE LISTING

SEQ ID NO:1—amino acid sequence of residues 25-567 of c-Met with an extra 3 amino acids at the N-terminus and an extra 9 amino acids at the C-terminus.

SEQ ID NO:2—amino acid sequence of an epitope corresponding to residues 121-130 of the human c-Met sequence and corresponding to the core epitope sequence of antibody LMH 82.

SEQ ID NO:3—amino acid sequence of an epitope corresponding to residues 216-230 of the human c-Met sequence and corresponding to the core epitope sequence of antibody LMH 84.

SEQ ID NO:4—amino acid sequence of an epitope corresponding to residues 236-245 of the human c-Met sequence and corresponding to the core epitope sequence of antibodies LMH 86, LMH 87, LMH 88 and LMH 89.

SEQ ID NO:5—amino acid sequence of an epitope corresponding to residues 521-541 of the human c-Met sequence and corresponding to the core epitope sequence of antibody LMH 81.

SEQ ID NO:6—amino acid sequence of an epitope corresponding to residues 521-535 of the human c-Met sequence and corresponding to the core epitope sequence of antibody LMH 80.

SEQ ID NO:7—amino acid sequence of the CDRH1 of antibody LMH 80.

SEQ ID NO:8—amino acid sequence of the CDRH2 of antibody LMH 80.

SEQ ID NO:9—amino acid sequence of the CDRH3 of antibody LMH 80.

SEQ ID NO:10—amino acid sequence of the CDRL1 of antibody LMH 80.

SEQ ID NO:11—amino acid sequence of the CDRL2 of antibody LMH 80.

SEQ ID NO:12—amino acid sequence of the CDRL3 of antibody LMH 80.

SEQ ID NO:13—amino acid sequence of the heavy chain variable region of antibody LMH 80.

SEQ ID NO:14—amino acid sequence of the light chain variable region of antibody LMH 80.

SEQ ID NO:15—amino acid sequence of the CDRH1 of antibody LMH 82.

SEQ ID NO:16—amino acid sequence of the CDRH2 of antibody LMH 82.

SEQ ID NO:17—amino acid sequence of the CDRH3 of antibody LMH 82.
SEQ ID NO:18—amino acid sequence of the CDRL1 of antibody LMH 82.
SEQ ID NO:19—amino acid sequence of the CDRL2 of antibody LMH 82.
SEQ ID NO:20—amino acid sequence of the CDRL3 of antibody LMH 82.
SEQ ID NO:21—amino acid sequence of the heavy chain variable region of antibody LMH 82.
SEQ ID NO:22—amino acid sequence of the light chain variable region of antibody LMH 82.
SEQ ID NO:23—amino acid sequence of the CDRH1 of antibody LMH 87.
SEQ ID NO:24—amino acid sequence of the CDRH2 of antibody LMH 87.
SEQ ID NO:25—amino acid sequence of the CDRH3 of antibody LMH 87.
SEQ ID NO:26—amino acid sequence of the CDRL1 of antibody LMH 87.
SEQ ID NO:27—amino acid sequence of the CDRL2 of antibody LMH 87.
SEQ ID NO:28—amino acid sequence of the CDRL3 of antibody LMH 87.
SEQ ID NO:29—amino acid sequence of the heavy chain variable region of antibody LMH 87.
SEQ ID NO:30—amino acid sequence of the light chain variable region of antibody LMH 87.
SEQ ID NO:31—amino acid sequence of the CDRH1 of antibody LMH 85.
SEQ ID NO:32—amino acid sequence of the CDRH2 of antibody LMH 85.
SEQ ID NO:33—amino acid sequence of the CDRH3 of antibody LMH 85.
SEQ ID NO:34—amino acid sequence of the CDRL1 of antibody LMH 85.
SEQ ID NO:35—amino acid sequence of the CDRL2 of antibody LMH 85.
SEQ ID NO:36—amino acid sequence of the CDRL3 of antibody LMH 85.
SEQ ID NO:37—amino acid sequence of the heavy chain variable region of antibody LMH 85.
SEQ ID NO:38—amino acid sequence of the light chain variable region of antibody LMH 85.
SEQ ID NO:39—nucleotide sequence of the heavy chain variable region of antibody LMH 87.
SEQ ID NO:40—nucleotide sequence of the light chain variable region of antibody LMH 87.
SEQ ID NO:41—nucleotide sequence of the heavy chain variable region of antibody LMH 85.
SEQ ID NO:42—nucleotide sequence of the light chain variable region of antibody LMH 85.

Selected Definitions

As used herein the term "antibody" refers to an immunoglobulin molecule capable of binding to a target through at least one epitope recognition site, located in the variable region of the immunoglobulin molecule. The term encompasses polyclonal and monoclonal antibodies, as well as variants, fusion proteins comprising an antibody portion with an epitope recognition site of the required specificity, humanized antibodies, human antibodies, chimeric antibodies and any other modified configuration of the immunoglobulin molecule that comprises an epitope recognition site of the required specificity.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" are any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J Immunol. Methods 242: 193-204 9 (2000)); and (xii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

As used herein the term "antigen-binding fragment" is taken to include an Fab, Fab', F(ab')$_2$, Fv, Fd, single-chain Fv (scFv), disulfide-linked Fvs (sdFv), V$_L$ and V$_H$ domain fragments, domain antibody, trispecific (Fab$_3$), bispecific (Fab$_2$), diabody ((V$_L$-V$_H$)$_2$ or (V$_H$-V$_L$)$_2$), triabody (trivalent), tetrabody (tetravalent), minibody ((scFv-CH$_3$)$_2$), bispecific single-chain Fv (Bis-scFv), IgGdeltaCH2, scFv-Fc and (scFv)$_2$-Fc. An "Fab fragment" consists of a monovalent antigen-binding fragment of an antibody molecule, and can be produced by digestion of a whole antibody molecule with the enzyme papain, to yield a fragment consisting of an intact light chain and a portion of a heavy chain. An "Fab' fragment" of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner. An "F(ab')2 fragment" of an antibody consists of a dimmer of two Fab' fragments held together by two disulfide bonds, and is obtained by treating a whole antibody with the enzyme pepsin, without subsequent reduction. An "Fv fragment" is a genetically engineered fragment containing the variable region of a light chain and the variable region of a heavy chain expressed as two chains. A "single chain antibody" (SCA) is a genetically engineered single chain molecule containing the variable region of a light chain and the variable region of a heavy chain, linked by a suitable, flexible polypeptide linker.

As used herein, "antibody variable region" refers to the portions of the light and heavy chains of antibody molecules that include amino acid sequences of complementarity determining regions (CDRs; i.e., CDR1, CDR2 and CDR3), and framework regions (FRs). V$_H$ refers to the variable region of the heavy chain. V$_L$ refers to the variable region of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)) or Chotia and Lesk 1987 *J. Mol Biol.* 196:901-917). Amino acid numbering of antibodies or antigen binding fragments is also according to that of Kabat. With regards to the antibodies of the present invention, determination of the complementarity determining regions was made using the IMGT numbering system (Lefranc, M-P et al., Nucleic Acids Research 27, 209-212 (1999)).

The term "antibody conjugate" as used herein refers to an antibody or antigen binding fragment thereof that includes a therapeutic agent or label attached thereto. The agent may be attached covalently or non-covalently or via a linker. The agent may be understood to encompass labels, including detectable or functional labels. Suitable therapeutic agents are described elsewhere in this document.

As used herein, the term "specifically binds" shall be taken to mean an antibody reacts or associates more frequently, more rapidly, with greater duration and/or with greater affinity with a particular cell or substance than it does with alternative cells or substances. It is also understood by reading this definition that, for example, an antibody that specifically binds to a first target may or may not specifically bind to a second target. As such, "specific binding" does not necessarily require exclusive binding or non-detectable binding of another molecule, this is encompassed by the term "selective binding". Generally, but not necessarily, reference to binding means specific binding.

As used herein, the terms "cell proliferative disorder" and grammatical variations thereof, when used in reference to a cell, tissue or organ, refers to any undesirable, excessive or abnormal cell, tissue or organ growth, proliferation, differentiation or survival. Undesirable cell proliferation disorders include diseases and physiological conditions, both benign hyperplastic conditions characterized by undesirable, excessive or abnormal cell numbers, cell growth, cell proliferation, cell survival or differentiation in a subject. Specific examples of such disorders include metastatic and non-metastatic neoplasia, tumors and cancers (malignancies).

The term "c-Met" as used herein is intended to refer to the c-Met receptor, a proto-oncogene and HGF/SF receptor, or to a portion of the c-Met receptor, including those portions of c-Met capable of binding HGF and those portions which have tyrosine kinase activity, or the c-Met receptor portion as set forth in SEQ ID NO:1. Preferably the term c-Met refers to human c-Met.

The term "chimeric antibody" refers to antibodies in which a portion of the heavy and/or light chain is identical with or homologous to corresponding sequences in antibodies derived from a particular species (e.g. murine) or belonging to a particular antibody class or subclass, while the remainder of the chain(s) is identical with or homologous to corresponding sequences in antibodies derived from another species (e.g. primate) or belonging to another antibody class or subclass, as well as fragments of such antibodies, so long as they exhibit the desired biological activity.

As used herein, the term "complementarity determining regions" (syn CDRs; i.e CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a CDR region as defined by Kabat (i.e. about residues 24-34 or 24-39 (LI)), 50-56 or 55-61 (L2) and 89-97 or 93-102 (L3) in the light chain variable domain and 31-35 or 26-35 (HI), 50-65 or 50-66 (H2) and 95-102 or 97-108 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" i.e. about residues 26-32 (LI), 50-52 (L2) and 91-96 (L3) in the light chain variable domain and 26-32 (HI), 53-55 (H2) and 96-101 (H3) in the heavy chain variable domain; Chothia and Lesk (1987) *J. Mol Biol.* 196:901-917). In some instances, a complementarity determining region can include amino acids from both a CDR region defined according to Kabat and a hypervariable loop. The skilled artisan will be aware of some variation in the positioning of the FRs, e.g., as a result of mutations (e.g., deletions and/or insertions), e.g., up to 5 residues variation, or 4 residues variation, or 2 residues variation, or 1 residue variation (e.g., as exemplified antibodies herein).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The terms "consisting of" or "consisting essentially of" refers to a peptide sequence of a defined number of residues which is not covalently attached to a larger product.

The term "constant region" (CR) as used herein, refers to the portion of the antibody molecule which confers effector functions. The constant regions of the subject humanized antibodies are derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Preferred heavy chain constant regions are gamma 1 (IgG1), gamma 2 (IgG2), gamma 3 (IgG3) and gamma 4 (IgG4). Light chain constant regions can be of the kappa or lambda type, preferably of the kappa type.

"Framework regions" (hereinafter FR) are those variable domain residues other than the CDR residues. Each variable domain of a naturally-occurring antibody typically has four FRs identified as FRI, FR2, FR3 and FR4.

The term "humanized antibody" shall be understood to refer to a chimeric molecule, generally prepared using recombinant techniques, having an epitope binding site derived from an immunoglobulin from a non-human species and the remaining immunoglobulin structure of the molecule based upon the structure and/or sequence of a human immunoglobulin. The antigen-binding site preferably comprises the complementarity determining regions (CDRs) from the non-human antibody grafted onto appropriate framework regions in the variable domains of human antibodies and the remaining regions from a human antibody.

The term "human antibody" as used herein in connection with antibody molecules and binding proteins refers to antibodies having variable (e.g. VH, VL, CDR and FR regions) and constant antibody regions derived from or corresponding to sequences found in humans, e.g. in the human germline or somatic cells.

The term "identity" and grammatical variations thereof, mean that two or more referenced entities are the same. Thus, where two antibody sequences are identical, they have the same amino acid sequence, at least within the referenced region or portion. Where two nucleic acid sequences are identical, they have the same polynucleotide sequence, at least within the referenced region or portion. The identity can be over a defined area (region or domain) of the sequence. The % identity of a polynucleotide is determined by GAP (Needleman and Wunsch, $J.$ $Mol$ $Biol.$ 48: 444-453.1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 100 nucleotides in length, and the GAP analysis aligns the two sequences over a region of at least 100 nucleotides. Most preferably, the two sequences are aligned over their entire length.

The term "isolated", including DNA, RNA or protein means a polynucleotide/polypeptide which is at least partially separated from the polynucleotide/polypeptide sequences with which it is associated or linked in its native state. Preferably, the isolated polynucleotide/polypeptide is at least 60% free, preferably at least 75% free, and most preferably at least 90% free from other components with which they are naturally associated.

The term "monoclonal antibody" refers to a homogeneous antibody population capable of binding to the same antigen(s) and, preferably, to the same epitopic determinant within the antigen(s). This term is not intended to be limited as regards to the source of the antibody or the manner in which it is made.

The term "nucleic acid" as used herein is used interchangeably with the term "polynucleotide".

The term "pharmaceutically acceptable" refers to molecular entities and compositions that are physiologically tolerable and do not typically produce an allergic or similar untoward reaction.

The term "subject" as used herein is intended to mean any animal, in particular mammals, particularly those animals or mammals which are agriculturally relevant, or veterinarily relevant, and/or which are commonly treated with pharmaceuticals or therapeutic agents or used in animal studies of pharmaceuticals or therapeutic agents, including and such as humans, horses, cows, pigs, cats and dogs, and may, where appropriate, be used interchangeably with the term "patient". Preferably, the subject is a primate. Particularly, the subject is a human.

The term "substantially as set out" it is meant that that CDR regions of the invention will be either identical or highly homologous to the specified regions of SEQ ID NOs: 7 to 12 or 15 to-20 or 23 to 28 or 31 to 36. By "highly homologous" it is contemplated that only a few substitutions, preferably from 1 to 4, or from 1 to 3 or 1 or 2 substitutions may be made in the CDRs.

The term "therapeutically effective amount" shall be taken to mean a sufficient quantity of an antibody or antigen-binding fragment to reduce or inhibit one or more symptoms of a cellular proliferation disorder to a level that is below that observed and accepted as clinically characteristic of that disorder. The skilled artisan will be aware that such an amount will vary depending on the specific antibody, fragment, and/or particular subject and/or type or severity or level of disease. Accordingly, this term is not to be construed to limit the invention to a specific quantity.

As used herein, the terms "treat," "treating," "treatment" and grammatical variations thereof mean subjecting an individual patient to a protocol, regimen, process or remedy, in which it is desired to obtain a physiologic response or outcome in that patient. Since every treated patient may not respond to a particular treatment protocol, regimen, process or remedy, treating does not require that the desired physiologic response or outcome be achieved in each and every patient or patient population. Accordingly, a given patient or patient population may fail to respond or respond inadequately to treatment.

The terms "tumor," or "cancer" are used interchangeably and refer to a cell or population of cells whose growth, proliferation or survival is greater than growth, proliferation or survival of a normal counterpart cell, e.g. a cell proliferative or differentiative disorder. Typically, the growth is uncontrolled.

DETAILED DESCRIPTION OF THE INVENTION

The present invention employs conventional molecular biology, microbiology and recombinant DNA techniques within the skill of the art. See for example, Sambrook et al "Molecular Cloning" A Laboratory Manual (1989).

The present invention is not to be limited in scope by the specific embodiments described herein, which are intended for the purpose of exemplification only.

Functionally Equivalent Antibodies

The present invention also contemplates antibodies or antigen-binding fragments thereof with one or more amino acid additions, deletions, or substitutions of the heavy and light chain variable region sequences of the antibodies of the invention but still retain the function of an antibody of the invention. These modifications may be deliberate, such as, for example through site-directed mutagenesis, or may be accidental such as those obtained through mutations in hosts that express the antibody.

Mutant (altered) polypeptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. Products derived from mutated/altered DNA can readily be screened using techniques described herein to determine if they have receptor-binding and/or -inhibitory activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the antibody and/or immunoglobulin chain molecule, including in the variable region, removed and a different residue inserted in its place. The sites of greatest interest for substitutional mutagenesis include sites identified as important for antigen binding. These sites, especially those falling within a sequence of at least three other identically conserved sites of human antibodies and/or immunoglobulin chains, are preferably substituted in a relatively conservative manner. Such conservative substitutions are shown in Table 1 under the heading of "exemplary substitutions".

Conservative amino acid substitutions are also contemplated by the present invention. These are taken to mean amino acid substitutions set forth in the following Table.

TABLE 1

Exemplary Substitutions

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe; ala |

The amino acids described herein are preferably in the "L" isomeric form. However, residues in the D isomeric form can be substituted for any L-amino acid residue, as long as the desired functional property of immunoglobulin binding is retained by the polypeptide. Modifications also include structural and functional analogues, for example, peptidomimetics having synthetic or non-natural amino acids or amino acid analogues and derivatized forms.

Antibody Generation

The general methodology for making monoclonal antibodies by hybridoma is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890. Panels of monoclonal antibodies produced against c-Met can be screened for various properties; i.e., isotype, epitope, affinity, etc. Of particular interest are monoclonal antibodies that mimic the activity of c-Met or its subunits. Such monoclonals can be readily identified in specific binding member activity assays. High affinity antibodies are also useful when immunoaffinity purification of native or recombinant specific binding member is possible. A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

The antibodies of the invention can also be produced by immunisation of an animal with a purified sema domain containing antigen and live c-Met expressing cells according to the invention. To the inventors knowledge such an immunisation strategy has not been previously described for generating anti c-Met antibodies.

Suitable techniques that additionally may be employed in antibody methods include affinity purification, non-denaturing gel purification, HPLC or RP-HPLC, size exclusion, purification on protein A column, or any combination of these techniques. The antibody isotype can be determined using an ELISA assay, for example, a human Ig can be identified using mouse Ig-absorbed anti-human Ig.

Recombinant Antibody Production

The antibodies and antigen-binding fragments of the invention can also be produced recombinantly using techniques and materials readily obtainable for example an automated peptide synthesis apparatus (see, e.g., Applied Biosystems, Foster City, Calif.).

The variable domains may be derived from any germline or rearranged human variable domain, or may be a synthetic variable domain based on consensus sequences of known human variable domains. The CDR-derived sequences of the invention, may be introduced into a repertoire of variable domains lacking CDR regions, using recombinant DNA technology. For example, Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking one or more CDR. Marks et al further describe how this repertoire may be combined with a CDR of a particular antibody. Using analogous techniques, the CDR-derived sequences of the present invention may be shuffled with repertoires of VH or VL domains lacking one or more CDR, and the shuffled complete VH or VL domains combined with a cognate VL or VH domain to provide antibodies of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members. Analogous shuffling or combinatorial techniques are also disclosed by Stemmer (Nature, 1994, 370:389-391), who describes the technique in relation to a β-lactamase gene but observes that the approach may be used for the generation of antibodies.

The antibodies may also be affinity matured using known selection and/or mutagenesis methods as are known in the art.

Recombinant antibodies of the invention can also be produced by phage display methodology such as that disclosed in U.S. Pat. No. 5,969,108.

Antibodies of the invention may further comprise antibody constant regions or parts thereof. For example antibodies based on SEQ ID NOs: 14, 22, 30 or 38 may be attached at their C-terminal end to antibody light chain constant domain including human CK or Cλ chains. Similarly, antibodies based on SEQ ID NOs: 13, 21, 29 or 37 may be attached at their C-terminal end to all or part of an immunoglobulin heavy chain derived from any antibody isotype, e.g. IgG, IgA, IgE, IgD and IgM and any of the isotype subclasses, particularly IgGI, IgG2b, and IgG4.

For recombinant production, the nucleic acid encoding an antibody of the invention is preferably isolated and inserted into a replicable vector for further cloning (amplification of the DNA) or for expression. DNA encoding the antibody is readily isolated or synthesized using conventional procedures (e.g., by using oligonucleotide probes that are capable of binding specifically to DNAs encoding the heavy and light chains of the antibody). Many vectors are available. The vector components generally include, but are not limited to, one or more of the following: a signal sequence, a sequence encoding an antibody of the present invention or fragment thereof (e.g., derived from the information provided herein), an enhancer element, a promoter, and a transcription termination sequence.

(i) Signal sequence component. The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, Ipp, or heat-stable enterotoxin II leaders. For yeast secretion the native signal sequence may be substituted by, e.g., the yeast invertase leader, a factor leader, or acid phosphatase leader, the *C. albicans* glucoamylasc leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the antibody.

(ii) Promoter component. Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S. D.) sequence operably linked to the DNA encoding the antibody.

Promoters are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2). CMV, bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

(iii) Enhancer element component. Transcription of a DNA encoding the antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv (1982) Nature 297: 17-18 on enhancing elements for activation of eukaryotic promoters. The enhancer may be spliced into the vector at a position 5' or 3' to the antibody-encoding sequence, but is preferably located at a site 5' from the promoter.

(iv) Transcription termination component. Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/1 1026 and the expression vector disclosed therein.

(v) Selection and transformation of host cells. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescens*, and *Shigella*, as well as Bacilli such as *B. subtilis* and *B. licheniformis, Pseudomonas* such as *P. aeruginosa*, and *Streptomyces*. One preferred *E. coli* cloning host is *E. coli* 294 (ATCC 31,446), although other strains such as *E. coli* B, *E. coli* X 1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common bakers yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-I variant of *Autographa californica* NPV and the Bm-5 strain of *Bombyx mori* NPV, and such viruses may be used as the virus herein according to the present invention, particularly for transfection of *Spodoptera frugiperda* cells.

Examples of useful mammalian host cell lines are monkey kidney CVI line transformed by SV40 (COS-7, ATCC CRL 1651); human embryonic kidney line (293 or 293 cells subcloned for growth in suspension culture, Graham et al. (1977) Gen Virol. 36:59); baby hamster kidney cells (BHK, ATCC CCL 10); Chinese hamster ovary cells (CHO, Urlaub et al. (1980) Proc. Natl. Acad. Sci USA 77:4216); mouse Sertoli cells (TM4, Mather (1980) Biol. Reprod. 23:243-251); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al. (1982) Annals N. Y. Acad. Sci. 383:44-68); MRC 5 cells; FS4 cells; and PER.C6™ (Crucell NV).

Chimeric Antibodies

Chimeric antibodies are made by recombinant means by combining the variable light and heavy chain regions (VL and VH), obtained from antibody producing cells of one species with the constant light and heavy chain regions from another. Typically chimeric antibodies utilize rodent or rabbit variable regions and human constant regions, in order to produce an antibody with predominantly human domains. For example, a chimeric antibody comprises a variable region from a mouse antibody as described herein according to any embodiment fused to a human constant region. The production of such chimeric antibodies is known in the art, and may be achieved by standard means (as described, e.g., in Morrison, *Science* 229:1202 (1985); Oi et al, *BioTechniques* 4:214 (1986); Gillies et al, (1989) *J. Immunol. Methods* 125:191-202; U.S. Pat. Nos. 5,807,715; 4,816,567 and 4,816,397). It is further contemplated that the human constant regions of chimeric antibodies of the invention may be selected from IgGI, IgG2, IgG3, IgG4, IgG5, IgG6, IgG7, IgG8, IgG9, IgGI0, IgG1I, IgG12, IgG13, IgG14, IgG15, IgG16, IgG17, IgG18 or IgG19 constant regions.

Humanized and Human Antibodies

The antibodies of the present invention may be humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al. (1986) Nature, 321:522-525; Riechmann et al. (1988) Nature, 332: 323-329; and Presta (1992) Curr Op Struct Biol, 2:593-59).

Methods for humanizing non-human antibodies are known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Jones et al. supra; Riechmann et al. supra; Verhoeyen et al. (1988) Science, 239:1534-1536), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter (1991) J Mol Biol, 227:381; Marks et al. (1991) J Mol Biol, 222:581). The techniques of Cole et al. and Boerner et al. are also suitable for the preparation of human monoclonal antibodies (Cole et al., Monoclonal Antibodies and Cancer Therapy, Alan R. Liss, p. 77 (1985) and Boerner et al. (1991) J Immunol, 147:86-95). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope (Jespers et al, Bio/technology 12:899-903 (1988)).

The antibodies may also be affinity matured using known selection and/or mutagenesis methods as are known in the art. Preferred affinity matured antibodies have an affinity which is five times, more preferably 10 times, even more preferably 20 or 30 times greater than the starting antibody (generally murine, humanized or human) from which the matured antibody is prepared.

Modified Antibodies

The glycosylation pattern of an antibody may be altered from the original glycosylation pattern of the reference antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Modified glycoforms of antibodies of the present invention may be useful for a variety of purposes, including but not limited to enhancing or reducing effector function and/or modifying half life of the antibody (see, for example, WO/2007/010401). Such alterations may result in a decrease or increase of C1q binding and CDC or of FcγR binding and ADCC. Substitutions can, for example, be made in one or more of the amino acid residues of the heavy chain constant region, thereby causing an alteration in an effector function while retaining the ability to bind to the antigen as compared with the modified antibody, cf. U.S. Pat. No. 5,624,821 and U.S. Pat. No. 5,648,260. Engineered glycoforms may be generated by any method known to one skilled in the art, for example by using engineered or variant expression strains, by co-expression with one or more enzymes, for example β(I,4)-N-acetylglucosaminyltransferase III (GnTII 1), by expressing an antibody or fragment thereof in various organisms or cell lines from various organisms, or by modifying carbohydrate(s) after the antibody or fragment has been expressed. Methods for generating engineered glycoforms are known in the art, and include but are not limited to those described in Umana et al, 1999, Nat. Biotechnol 17:176-180; Davies et al., 2007 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140AI; PCT WO 02/30954A1; Potelligent® technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49.

It may be desirable to modify the antibody of the invention with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1 191-1 195 (1992) and Shopes, B. J. Immunol. 148: 2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. D. Alternatively, the antibody half-life may be increased by pegylation.

Antibody Conjugates

The present invention also provides antibodies and antigen-binding fragments herein according to any embodiment conjugated to an agent or detectable label. The label can include for example, a detectable or functional label. The therapeutic agent can include a cytotoxin, or an anti-neoplastic agent. The detectable label may comprise a radioisotope (e.g., iodine-131, yttrium-90 or indium-111, $C^{14}$, $S^{35}$, $P^{32}$, $P^{33}$, $H^3$, $I^{125}$, $I^{131}$, gallium-67 and 68, scantium-47, lutitium-177, radium-223).

A cytotoxin includes any agent that is detrimental to (e.g., kills) cells. For a description of these classes of drugs which are known in the art, and their mechanisms of action, see Goodman et al., Goodman and Gilman's The Pharmacological Basis of Therapeutics, 8th Ed., Macmillan Publishing Co., 1990. Additional techniques relevant to the preparation of antibody immunotoxins are provided in for instance Vitetta (1993) and U.S. Pat. No. 5,194,594. Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *saponaria officinalis* inhibitor, gelonin, mitogellin, restrictocin, phenomycin, enomycin and the tricothecenes. See, for example, WO 93/21232.

Suitable anti-neoplastic agents according to the invention include taxol, cytochalasin B, gramicidin D, ethidium bromide, emetine, gefitinib mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)).

Labels also include fluorescent labels, for example biotin-streptavidin, horseradish peroxidise urease, catalase, alkaline phosphatase, beta-galactosidase, and chloramphenicol transferase.

Suitable detectable labels include T7-, His-, myc-, HA- and FLAG-tags; electron-dense reagents; energy transfer molecules; paramagnetic labels; fluorophores (fluorescein, rhodamine, phycoerythrin); chromophores; chemi-luminescent (imidazole, luciferase); and bio-luminescent agents.

Antibodies of the invention may be labelled with a detectable or functional label. Detectable labels include, but are not limited to, radiolabels such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{121}$I, $^{124}$I, $^{125}$I, $^{131}$I, $^{111}$In, $^{117}$Lu, $^{211}$At, $^{198}$Au, $^{67}$Cu, $^{225}$Ac, $^{213}$Bi, $^{99}$Tc and $^{186}$Re, which may be attached to antibodies of the invention using conventional chemistry known in the art of antibody imaging. Labels also include fluorescent labels (for example fluorescein, rhodamine, Texas Red) and labels used conventionally in the art for MRI-CT imaging. They also include enzyme labels such as horseradish peroxidase, β-glucoronidase, β-galactosidase, urease. Labels further include chemical moieties such as biotin which may be detected via binding to a specific cognate detectable moiety, e.g. labeled avidin. Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

Also, antibodies including fragments thereof, and drugs that modulate the production or activity of the specific binding members, antibodies and/or their subunits may possess certain diagnostic applications and may for example, be utilized for the purpose of detecting and/or measuring conditions such as cancer, precancerous lesions, conditions related to or resulting from hyperproliferative cell growth or the like. For example, the specific binding members, antibodies or their subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the specific binding members of the invention may be discovered or synthesized, and may be used in diagnostic and/or therapeutic protocols.

The radiolabeled specific binding members, particularly antibodies and fragments thereof, are useful in in vitro diagnostics techniques and in in vivo radioimaging techniques and in radioimmunotherapy. In the instance of in vivo imaging, the specific binding members of the present invention may be conjugated to an imaging agent rather than a radioisotope(s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanium, holmium and ferbium. In a further aspect of the invention, radiolabeled specific binding members, particularly antibodies and fragments thereof, particularly radioimmunoconjugates, are useful in radioimmunotherapy, particularly as radiolabeled antibodies for cancer therapy. In a still further aspect, the radiolabeled specific binding members, particularly antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

Radioimmunotherapy (RAIT) has entered the clinic and demonstrated efficacy using various antibody immunoconjugates. $^{131}$I labeled humanized anti-carcinoembryonic antigen (anti-CEA) antibody hMN-14 has been evaluated in colorectal cancer (Behr T M et al (2002) Cancer 94(4Suppl):1373-81) and the same antibody with $^{90}$Y label has been assessed in medullary thyroid carcinoma (Stein R et al (2002) Cancer 94(1):51-61). Radioimmunotherapy using monoclonal antibodies has also been assessed and reported for non-Hodgkin's lymphoma and pancreatic cancer (Goldenberg D M (2001) Crit Rev Oncol Hematol 39(1-2):195-201; Gold D V et al (2001) Crit Rev Oncol Hematol 39 (1-2) 147-54). Radioimmunotherapy methods with particular antibodies are also described in U.S. Pat. Nos. 6,306,393 and 6,331,175. Radioimmunoguided surgery (RIGS) has also entered the clinic and demonstrated efficacy and usefulness, including using anti-CEA antibodies and antibodies directed against tumor-associated antigens (Kim J C et al (2002) Int J Cancer 97(4):542-7; Schneebaum S et al (2001) World J Surg 25(12):1495-8; Avital S et al (2000) Cancer 89(8):1692-8; McIntosh D G et al (1997) Cancer Biother Radiopharm 12 (4):287-94).

Animal Models

In vivo animal models of cancer or animal xenograft studies may be utilized by the skilled artisan to further or additionally screen, assess, and/or verify the antibodies or fragments thereof of the present invention, including further assessing c-Met modulation, c-Met down-regulation and/or inhibiting c-Met activation/tk activity in vivo and inhibiting tumor progression and/or infiltration. Such animal models include, but are not limited to models of c-Met mediated cancer or xenografts of c-Met activated or overexpressing cells (such as renal cell carcinomas). An exemplary and suitable model is U87 MG mouse xenograft models of glioblastoma, which is among several tumor cell lines that express both HGF and c-Met (Guerin C et al (2000) Biochem Biophys Res Commun 273:287-293; Tseng J R et al (2008) J Nucle Med 49(1):129-134).

Competitive Inhibition

Antibodies that competitively inhibit the binding of an LMH antibody of the invention to an epitope can be screened and identified using conventional competition binding assays known in the art. Numerous types of competitive binding assays are known, for example, solid phase direct or indirect radioimmunoassay (RIA), solid phase direct or indirect enzyme immunoassay (EIA), sandwich competition assay (see Stahli et al., Methods Enzymol, 92: 242-253, (1983); Kim et al., Infect. Immun. 57:944, (1989)); solid phase direct biotin-avidin EIA (see Kirkland et al., J Immunol, 137: 3614-3619 (1986)); solid phase direct labelled assay, solid phase direct labeled sandwich assay (see Harlow and Lane, Antibodies: A Laboratory Manual, Cold Spring Harbor Press, 1988); solid phase direct label RIA using $^{125}$I label (see Morel et al., Curr Stud Hematol Blood Transfus, 55: 53-63, (1988)); solid phase direct biotin-avidin EIA (Cheung et al., Virology 176:546, (1990)); or direct labelled RIA (Moldenhauer et al., Scand J Immunol, 32: 77-82, (1990)). see, for example, Harlow and Lane, 1988).

Typically such an assay involves the use of purified antigen bound to a solid surface, an unlabeled test protein and a labeled reference protein. Competitive inhibition is measured by determining the amount of label bound to the solid surface in the presence of the test protein.

Compositions of the Invention

Antibodies of the present invention will usually be administered in the form of a pharmaceutical composition, which may comprise at least one component in addition to the antibody or antigen-binding fragment thereof. Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

In some embodiments, liposomes and/or nanoparticles may also be employed with the active ingredients. The formation and use of liposomes is generally known to those of skill in the art. Liposomes can be formed from phospholipids that are dispersed in an aqueous medium and spontaneously form multilamellar concentric bilayer vesicles (also termed multilamellar vesicles (MLVs)). MLVs can generally have diameters of from 25 nm to 4 µm. Sonication of MLVs results in the formation of small unilamellar vesicles (SUVs) with diameters in the range of 200 to 500 angstrom, containing an aqueous solution in the core. Phospholipids can form a variety of structures other than liposomes when dispersed in water, depending on the molar ration of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state.

A composition may be administered alone or in combination with other treatments, therapeutics or agents, either simultaneously or sequentially dependent upon the condition to be treated. In addition, the present invention contemplates and includes compositions comprising the antibody or fragment thereof herein described and other agents or therapeutics such as anti-cancer agents or therapeutics, hormones, anti-EGFR agents or antibodies, anti-c-Met agents or antibodies, anti-HGF agents e.g. AMG-102, angiogenesis inhibitors or immune modulators. More generally these anti-cancer agents may be tyrosine kinase inhibitors or phosphorylation cascade inhibitors, post-translational modulators, cell growth or division inhibitors (e.g. anti-mitotics), or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. The composition can be administered in combination (either sequentially (i.e. before or after) or simultaneously) with tyrosine kinase inhibitors (including, but not limited to AG1478 and ZD1839, ST1571, OSI-774, SU-6668), doxorubicin, temozolomide, cisplatin, carboplatin, nitrosoureas, procarbazine, vincristine, hydroxyurea, 5-fluoruracil, cytosine arabinoside, cyclophosphamide, epipodophyllotoxin, carmustine, lomustine, and/or other chemotherapeutic agents. Thus, these agents may be anti-EGFR specific agents, or tyrosine kinase inhibitors such as AG1478, ZDI 839, STI571, OSI-774, or SU-6668 or may be more general anti-cancer and anti-neoplastic agents such as doxorubicin, cisplatin, temozolomide, nitrosoureas, procarbazine, vincristine, hydroxyurea, 5-fluoruracil, cytosine arabinoside, cyclophosphamide, epipodophyllotoxin, carmustine, or lomustine. In addition, the composition may be administered with hormones such as dexamethasone, immune modulators, such as interleukins, tumor necrosis factor (TNF) or other growth factors or cytokines which stimulate the immune response and reduction or elimination of cancer cells or tumors.

Antibodies of the present invention may be administered to a patient in need of treatment via any suitable route, usually by injection into the bloodstream or CSF, or directly into the site of the tumor. The precise dose will depend upon a number of factors, including whether the antibody is for diagnosis or for treatment, the size and location of the tumor, the precise nature of the antibody (whether whole antibody, fragment, diabody, etc), and the nature of the detectable or functional label attached to the antibody. Where a radionuclide is used for therapy, a suitable minimum single dose is about 45 mCi/$m^2$, to a maximum of about 250 mCi/$m^2$. Preferable dosage is in the range of 15 to 40 mCi, with a further preferred dosage range of 20 to 30 mCi, or 10 to 30 mCi. Such therapy may require bone marrow or stem cell replacement. A typical antibody dose for either tumor imaging or tumor treatment will be in the range of from 0.5 to 40 mg, preferably from 1 to 4 mg of antibody in F(ab')2 form. Naked antibodies are preferable administered in doses of 20 to 1000 mg protein per dose, or 20 to 500 mg protein per dose, or 20 to 100 mg protein per dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

Examples of suitable angiogenesis inhibitors (anti-angiogenic agents) include, but are not limited to, urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF, bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents. Other examples of inhibitors of angiogenesis, neovascularization, and/or other vascularization are anti-angiogenic heparin derivatives and related molecules (e.g., heperinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

Measuring Cell Viability

Cell toxicity and viability (cell apoptosis, lysis, growth proliferation, etc.) can be measured in a variety of ways on the basis of calorimetric, luminescent, radiometric, or fluorometric assays known in the art. Colorimetric techniques for determining cell viability include, for example, Trypan Blue exclusion (see, for example, Examples 1 and 2). In brief, cells are stained with Trypan Blue and counted using a hemocytometer. Viable cells exclude the dye whereas dead and dying cells take up the blue dye and are easily distinguished under a light microscope. Neutral Red is adsorbed by viable cells and concentrates in cell lysosomes; viable cells can be determined with a light microscope by quantitating numbers of Neutral Red stained cells.

Fluorometric techniques for determining cell viability include, for example, propidium iodide, a fluorescent DNA intercalating agent. Propidium iodide is excluded from viable cells but stains the nucleus of dead cells. Flow cytometry of propidium iodide labeled cells can then be used to quantitate viable and dead cells. Release of lactate dehydrogenase (LDH) indicates structural damage and death of cells, and can be measured by a spectrophotometric enzyme assay. Bromodeoxyuridine (BrdU) is incorporated into newly synthesized DNA and can be detected with a fluorochrome-labeled antibody. The fluorescent dye Hoechst 33258 labels DNA and can be used to quantitate proliferation of cells (e.g., flow cytometry). Quantitative incorporation of the fluorescent dye carboxyfluorescein diacetate succinimidyl ester (CFSE or CFDA-SE) can provide cell division analysis (e.g., flow cytometry). This technique can be used either in vitro or in vivo. 7-aminoactinomycin D (7-AAD) is a fluorescent intercalator that undergoes a spectral shift upon association with DNA, and can provide cell division analysis (e.g., flow cytometry).

Radiometric techniques for determining cell proliferation include, for example, [$^3$H]-Thymidine, which is incorporated into newly synthesized DNA of living cells and frequently used to determine proliferation of cells. Chromium ($^{51}$Cr)-release from dead cells can be quantitated by scintillation counting in order to quantitate cell viability.

Luminescent techniques for determining cell viability include, for example, the CellTiter-Glo luminescent cell viability assay (Promega Madison Wis.). This technique quantifies the amount of ATP present to determine the number of viable cells.

Commercially available kits for determining cell viability and cell proliferation include, for example, Cell Proliferation Biotrak ELISA (Amersham Biosciences Piscataway, N.J.); the Guava ViaCount™ Assay, which provides rapid cell counts and viability determination based on differential uptake of fluorescent reagents (Guava Technologies, Hayward, Calif.); the CyQUANT™ Cell Proliferation Assay Kit (Molecular Probes, Inc., Eugene, Oreg.); and the CytoLux Assay Kit (PerkinElmer Life Sciences Inc., Boston, Mass.). The DELFIA™ Assay Kits (PerkinElmer Life Sciences Inc., Boston, Mass.) can determine cell proliferation and viability using a time-resolved fluorometric method. The Quantos™ Cell Proliferation Assay is a fluorescence-based assay that measures the fluorescence of a DNA-dye complex from lysed cells (Stratagene, La Jolla, Calif.). The CellTiter-Glo cell viability assay is a luminescent assay for measuring cell viability (Promega, Madison Wis.).

Uses

The antibodies of the present invention are useful in a variety of applications, including research, diagnostic and therapeutic applications.

The antibodies described herein can act as inhibitors to inhibit (which can be reducing or preventing) (a) binding (e.g., of a ligand, an inhibitor) to the c-Met receptor, (b) a receptor signaling function, and/or (c) a stimulatory function. Antibodies which act as inhibitors of c-Met receptor function can block ligand binding directly or indirectly (e.g., by causing a conformational change). For example, antibodies can inhibit c-Met receptor function by inhibiting binding of a ligand, or by desensitization (with or without inhibition of binding of a ligand).

In one aspect, the present invention provides a method of treating or preventing a disorder in a subject. As used herein, a "disorder" is a disruption of or interference with normal function.

Diagnostic Assays

The present invention also relates to a variety of diagnostic applications, including methods for detecting the presence of stimuli such as aberrantly expressed c-Met, by reference to their ability to be recognized by an antibody of the invention. Diagnostic applications of the antibody(ies) of the present invention include in vitro and in vivo applications well known and standard to the skilled artisan and based on the present description. Diagnostic assays and kits for in vitro assessment and evaluation of c-Met status, particularly with regard to aberrant expression of c-Met, may be utilized to diagnose, evaluate and monitor patient samples including those known to have or suspected of having cancer, a precancerous condition, a condition related to hyperproliferative cell growth or from a tumor sample. The assessment and evaluation of c-Met status is also useful in determining the suitability of a patient for a clinical trial of a drug or for the administration of a particular chemotherapeutic agent or specific binding member, particularly an antibody, of the present invention, including combinations thereof, versus a different agent or antibody. This type of diagnostic monitoring and assessment is already in practice utilizing antibodies against the HER2 protein in breast cancer (Hercep Test, Dako Corporation), where the assay is also used to evaluate patients for antibody therapy using Herceptin. In vivo applications include imaging of tumors or assessing cancer status of individuals, including radioimaging.

The presence of c-Met in cells can be ascertained in vitro or in vivo immunological procedures known to persons skilled in the art. For example, the c-Met receptor forms complexes with one or more antibody(ies) and one member of the complex is labeled with a detectable label. The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. The anti c-Met antibody can also be labeled with a radioactive element or with an enzyme. The radioactive label can be detected by any of the currently available counting procedures. The preferred isotope may be selected from $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{121}$I, $^{124}$I, $^{125}$I, $^{131}$I$_{5}$ $^{111}$In, $^{211}$At, $^{198}$Au, $^{67}$Cu, $^{225}$Ac, $^{213}$Bi, $^{99}$Tc and $^{186}$Re. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

The invention also contemplates the use of therapeutic or diagnostic kits comprising an antibody of the invention for use in the present treatment methods. Such kits will generally contain, in suitable container means, a pharmaceutically acceptable formulation of at least one LMH antibody or fragment of the present invention. The kits can be used in detecting the presence of a c-Met receptor in a biological sample. The antibody compositions of the present invention can be provided in liquid or lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the antibody is employed, such antibody can be provided in the kit, for instance in a separate vial or container. The second antibody, if present, is typically labeled, and can be formulated in an analogous manner with the antibody formulations described herein.

Tumor Cells

A tumor cell according to the invention is any cell in which c-Met is expressed. These include carcinomas, for example bladder, breast, cervical, cholangiocarcinoma, colorectal, endometrial, esophogeal, gastric, head and neck, kidney, liver, lung, nasopharyngeal, ovarian, pancreas, prostate and thyroid; musculoskeletal sarcomas, for example, osteosarcoma, rhabdomyosarcoma and synovial sarcoma; soft tissue sarcomas for example Kaposi's sarcoma, leiomyosarcoma and fibrosarcoma; hematopoietic malignancies, for example, T cell leukemia, lymphomas and multiple myeloma; and other neoplasms for example, glioblastomas, melanoma, mesothelioma, and Wilms Tumor.

Aptamers

It will also be appreciated that the c-Met epitope sequences described herein can be targeted using aptamers. A nucleic acid aptamer (adaptable oligomer) is a nucleic acid molecule that is capable of forming a secondary and/or tertiary structure that provides the ability to bind to a molecular target. Methods for aptamer generation are known in the art, and may be prepared using methods generally disclosed by Mascini (*Aptamers in Bioanalysis*, John Wiley & Sons Inc, 2009). An aptamer library is produced, for example, by cloning random oligonucleotides into a vector (or an expression vector in the case of an RNA aptamer), wherein the random sequence is flanked by known sequences that provide the site of binding for PCR primers. An aptamer with increased activity is selected, for example, using SELEX (Systematic Evolution of Ligands by EXponential enrichment). Suitable methods for producing and/or screening an aptamer library are described, for example, in Elloington and Szostak, Nature 346:818-22, 1990.

Accordingly, the invention also relates to a nucleic acid aptamer that specifically binds to an epitope sequence of c-Met described herein. Such aptamers can be used to target c-Met for the treatment of cellular proliferative diseases described herein.

Deposit Statement

The hybridoma cell line producing the monoclonal antibody LMH 80 was received by the American Type Culture Collection (ATCC) 10801 University Boulevard, Manassas, Va. on 14 Oct. 2010. The hybridoma was assigned patent deposit designation PTA-11405. The hybridoma cell line producing the monoclonal antibody LMH 82 was received by the American Type Culture Collection (ATCC) 10801 University Boulevard, Manassas, Va. on 14 Oct. 2010. The hybridoma was assigned patent deposit designation PTA-11406. The deposits will be made available in accordance with the requirements under the Budapest Treaty. However, it should be understood that the availability of a deposit does not constitute a license to practice the subject invention in derogation of patent rights granted by governmental action. Further, the subject culture deposits will be stored and made available to the public in accordance with the provisions of the Budapest Treaty for the Deposit of Microorganism i.e. they will be stored with all the care necessary to keep them viable and uncontaminated for a period of at least five years after the most recent request for furnishing of a sample of the deposits, and in any case, for a period of at least 30 (thirty) years after the date of deposit or for the enforceable life of any patent which may issue disclosing the cultures pus five years after the last request for a sample from the deposit. The depositor acknowledges the duty to replace the deposit should the depository be unable to furnish a sample when requested, due to the condition of the deposits.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The present invention is described further in the following non-limiting examples.

Example 1

Materials and Methods 1.1 Cells

The lung adenocarcinoma cell line A549 (ATCC #CCL-185) and the glioma cell line U87MG (ATCC #HTB-14) were all obtained from the American Type Culture Collection (ATCC, USA). All cell lines were cultured at 37° C., 5% $CO_2$ in DMEM/F12 medium containing 5% FCS and 5 mM Glutamax (Invitrogen, Melbourne, Australia). SK-OV-3 human ovarian carcinoma cells were obtained from ATCC, (ATCC Number: HTB-77).

1.2 Immunization Protocol and Antibody Production

The human lung carcinoma cell line A549 was used to immunize mice in combination with a purified truncated c-Met fragment designated 25-567H (SEQ ID NO:1). A549 cells comprise an autoactived c-Met receptor and hence constitutively overexpress c-Met. These cells also include some unprocessed form of the c-Met receptor. The truncated c-Met fragment used for immunization was derived from CHO-Lec cells transfected with a construct comprising residues 25-567 of c-Met further containing an extra 3 amino acids in the N-terminus (ETR) and an extra 9 amino acids (including a $His_6$ terminal tag) at the C-terminus for cloning in frame with an Ig leader sequence (N-terminus) and for purification (C-terminus). The transfected CHO-Lec cells were provided by Dr Ermanno Gherardi (Cambridge University Medical School, MRC Centre, United Kingdom).

Mouse hybridomas were generated by immunizing BALB/c mice four to five times intraperitoneally (i.p.) at 4 week intervals with $2\times10^6$ lysed A549 cells or purified truncated recombinant c-Met antigen in Freund's adjuvant (Sigma) following an initial immunization in Complete Freund's adjuvant (Sigma) as indicated by the tabled immunization protocols. Incomplete Freund's adjuvant was used for subsequent immunisations. The immunization protocol is described in Table 1 below.

| Immunization Procedures for different clones | | | |
|---|---|---|---|
| Immunization Protocol C-Met Ag (Ag): 30 µg/time A549 Cells (C): 2 × 10⁶/time | Positive clones Based on ELISA with c-Met Ag | Further test on FACS A549 cells | LMH clones |
| Ag + C + C + Ag +Ag | 128 | 21 | 80, 81, 82 |
| Ag + C + C + Ag + Ag | 118 | 6 | 83, 84 |
| Ag + C + C + Ag + Ag | 126 | 37 | 86-89 |
| Ag + C + C + C + Ag + Ag | 61 | 192 | 85 |

LMH = laboratory designation for the antibodies

Spleen cells from immunized mice were fused with mouse myeloma cell line SP2/0. Supernatants from newly generated clones were screened by ELISA for specific reactivity with recombinant c-Met antigen as described below. Positive supernatants were then screened for binding to the c-Met receptor on A549 cells by flow cytometry as described below. Antibody was purified from supernatants of positive clones using protein-A affinity chromatography according to standard methods.

1.3 ELISA Assay

For the ELISA assay, the wells of an Elisa plate (Nunc MaxiSorp 446612) were coated with 50 µl of 3 µg/ml of c-Met antigen in 0.05 M PBS buffer pH 7.2, overnight at 4° C. Following incubation, the supernatant was removed and the wells washed twice with wash buffer 0.05% Tween20-PBS, this was followed by a 1 hour block at room temperature with 3% FCS/PBS at 230 µl/well. The wells were then washed one with wash buffer (0.05% Tween 2-PBS) and rinsed with PBS. 100 µl of sample (hybridoma supernatant) was then added to each well and the plate incubated at room temperature for 1 hour. This was followed by a 4× wash with wash buffer (0.05% Tween 2-PBS) and rinse with PBS. 100 µl of goat anti-mouse Ig gamma-AP (Sigma A3438), diluted in wash buffer 1:2000 was then added and allowed to incubate at room temperature for 1 hour. Following the incubation, the wells were washed 4× with wash buffer and rinsed with PBS. The reaction was developed with 100 µl of pNPP (1 mg/ml n diethanolamine-HCL buffer pH 9.6) for 10 mins at room temperature. This was followed by stop solution (3.0 M NaOH, 50 µl/well). The OD was measured at 405 nm.

The reagents were prepared as follows:

Conjugate:

Goat anti-mouse Ig (whole)-Alkaline phosphatase (Sigma A-3688 Lot 69H9207)

1:3000 dilution in 1% FCS/PBS, 100 µl/well, room temperature 1 hour

Substrate:

pNPP (p-Nitrophenyl Phosphate; ICN Cat No. 151766; Lot No. 6909C, storage −20° C.)

1 mg/ml in diethanolamine-HCl (0.1M) and $MgCl2.6H2O$ buffer

100 µl/well, room temperature 10 minutes 1.4 Flow Cytometry $5\times10^5$ A549 cells were incubated with antibody LMH 85 or antibody LMH 87 (10 µg/ml) and bound antibody was detected using PE-conjugated anti-mouse antibody. The control antibody was a mouse IgG1 isotype matched antibody. An increase in PE signal intensity indicated antibody binding to c-Met.

1.5 SKOV-3 Cell Migration Assay

Antibodies were tested for their ability to stimulate or inhibit cell migration in a Neuro Probe A-Series 96-well Chemotaxis Chamber with framed 8 μm membrane coated with collagen. The ovarian carcinoma cells SK-OV-3, were used for all assays. Bottom wells of the chamber were filled with antibodies at desired concentration, diluted in RPMI with 0.25% BSA. For antagonist tests, 0.3 pM HGF was mixed with the antibody. The top of the chamber was filled with $4 \times 10^5$ SK-OV-3 cells in RPMI/0.25% BSA. After 4 hour incubation in a 37° C. incubator, the membrane was recovered migrated cells fixed with 4% formaldheyde for 1 h, washed with PBS and stained over night with DeepRed Cytoplasmic Stain (InVitrogen). The membranes were scanned using a LiCor Odessey Infrared scanner at 700 nm and cells counted.

1.6 Epitope Mapping

A PepSet™ Peptide library spanning amino acids 1-567 of c-Met (including the SEMA domain) was synthesized (Mimotopes, Clayton, Australia). The library consisted of N-terminally biotinylated, 20-mer peptides, overlapping by 15 amino acids and pre-absorbed onto 96-well streptavidin coated plates. LMH antibodies 80 to 89 were added to these plates to determine their reactivity against each single peptide using standard ELISA. Epitopes for each antibody were determined by overlaying the sequences of the peptides which reacted with the antibody, leading to a determination of a core common amino acid sequence.

1.7 Western Analysis

Cells were plated at $2 \times 10^5$/well in 6-well plates and incubated for 8 h, 37° C., 5% $CO_2$. Medium was removed and cells washed twice in PBS and once in serum free medium before serum starvation for 16 h. For agonist and antagonist assays, 50 μg/ml of each antibody was added and cells incubated at 37° C., 5% $CO_2$ for 45 min. Afterward, for antagonist tests only, 400 ng/ml of HGF was added to the media immediately and cells incubated for a further 7 min. For c-Met downregulation assays, 50 μg/ml of each antibody was added and cells incubated for 8 h. After treatments, cells were lysed in Triton X-100 cell lysis buffer, processed and c-Met immunoprecipitated as previously described (Pillay et al, 2009).

Protein samples were separated on 4-12% Bis-Tris gradient gels (Invitrogen) and gels soaked for 20 min in equilibration buffer [2×MES buffer (Invitrogen), 10% methanol, 1:1000 NuPage anti-oxidant (Invitrogen) and dd$H_2$O] at 22° C. Pre-equilibrated gels were transferred to PVDF membranes using the iBlot dry transfer system (Invitrogen). All membrane blocking and antibody incubation steps were conducted in Odyssey buffer (LI-COR Biosciences, Lincoln, Nebr.). Total c-Met was detected by probing with either the Met (25H2) mouse mAb (Cell Signaling Technology, Danvers, Mass.) or the rabbit polyclonal to Met (c-Met) antibody (Abcam, Cambridge, UK). Phosphorylated c-Met was detected by probing with the phospho-Met (Tyr1234/1235) (3D7) rabbit mAb (Cell Signaling Technology). The secondary antibody used for detection was the IRDye CW800-conjugated affinity purified anti-rabbit IgG antibody (Rockland Immunochemicals, Gilbertsville, Pa.). Western blots were analysed using the Odyssey Infrared Imaging System (LI-COR Biosciences).

1.8 xCELLigence

All tests were conducted in DMEM/F12 containing 0.5% FCS and 5 mM Glutamax (Invitrogen). A549 cells were plated in untreated E-plates (Roche Diagnostics, Basel, Switzerland) at 5,000 cell per well and U87MG cells were plated in E-plates pretreated with 1:50 Matrigel (BD Biosciences, Franklin Lakes, N.J.) at 40,000 cell per well. The plate was connected to an xCELLigence RTCA SP instrument (Roche Diagnostics) within a humidified cell incubator at 37° C., 5% $CO_2$. The following analysis program on the RTCA Software 1.2 (Roche Diagnostics) was used to collect the data on cellular growth. Firstly, 180 sweeps at 1 min intervals followed by 999 sweeps at 30 min intervals was initiated. After 21 h of growth for A549 cells and 48 h growth for U87MG cells, this program was aborted and the antibody treatments were added directly to cells. A second program of 180 sweeps at 1 min intervals followed by 999 sweeps at 30 min intervals was then conducted until termination after 60 h for A549 cells and 120 h for U87MG cells. Data was analysed using the RTCA Software 1.2 program (Roche Diagnostic). Readings were normalized to the point directly before antibody addition. All data is presented as the mean cellular index±SEM over time.

1.9 U87MG Xenograft Trial

U87MG xenograft trials were conducted essentially as previously described [Pillay et al, 2009]. Briefly, $1 \times 10^6$ cells were injected into the ventral left and right flanks of 4- to 6-week old female BALB/c nude mice. Treatment was initiated when tumor sizes reached 100 mm$^3$. An intraperitoneal (i.p.) route of administration was used after which tumor measurement and statistical analysis were done as previously described [Pillay et al, 2009]. This project was approved by the Monash University Animal Ethics Committee.

1.10 Biocore Analysis of Anti-c-Met Antibodies

Affinity of the LMH antibodies was determined by BIAcore analysis as described in detail (Nieba L et al., 1997). Briefly, a NTA sensor chip was loaded with Ni$^{2+}$ and used to immobilize His6-c-Met (the 25-567 fragment). The LMH antibodies were passed over the chip at varying concentrations in order to determine apparent affinity ($K_D$). Chips were regenerated with EDTA.

1.11 Method for Cell Surface Down-Regulation

A549 cells were plated overnight and washed twice in serum free medium before 24 hour treatments in serum free medium were added. The next day, antibody was added to the 8 hour treatments using the medium from the dish. At treatment completion, dishes were washed three times with excess PBS pH 8.0. Next, 0.5 mg/ml non-permeating EZ-Link® Sulfo-NHS-LC-Biotin (Thermo Scientific) in PBS pH 8.0 was added and cells rocked at 4° C. for 1 hour. Cells were quenched three times in excess 100 mM glycine. For immunoprecipitation (IP) of c-Met, cells were lysed by adding Triton X-100 cell lysis buffer [30 mM HEPES, pH7.4, 150 mM NaCl, 1% Triton X-100, 10 mM NaF, Calbiochem Protease Inhibitor Cocktail Set I, 200 μM Na$_3$VO$_4$ and 0.4% (v/v) $H_2O_2$] and incubating on ice for 20 min. The lysates were then clarified by centrifugation at 4° C. and immunoprecipitated using anti-c-Met beads (Santa Cruz). Following SDS-PAGE and transfer, membranes were probed for biotinylated c-Met using Streptavidin conjugated to IRDye 680 (LiCor Biosciences) or total c-Met using rabbit anti-Met (1000-1100) polyclonal antibody (Abcam) followed by anti-rabbit IRDye800 secondary. Blots were developed using infrared detection.

Results

Example 2

Characterisation of the Anti-C-Met Antibodies

Figure 1:
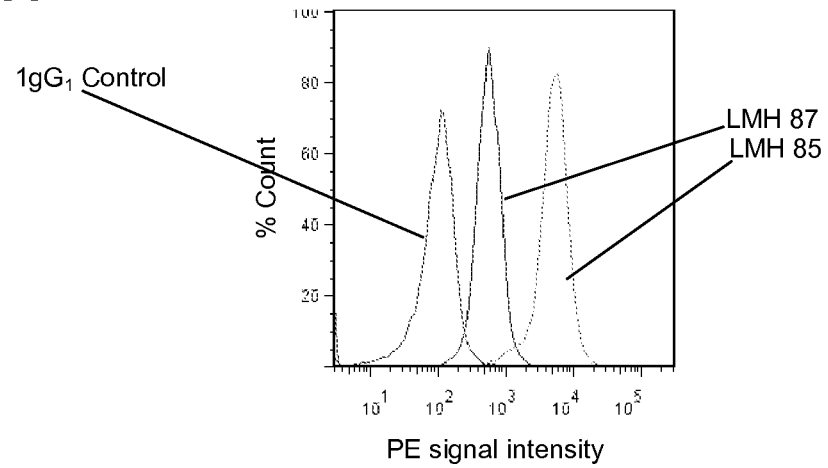
FIG. 1 Representative data showing biochemical characterization of the LMH antibody panel. (A) Flow cytometry analysis showing antibodies LMH 85 and LMH 87 bind surface c-Met expressed on A549 cells. The far left histogram represents an IgG1 isotype control. (B) Immunoblot showing c-Met α-chain specificity. Total c-Met was immunoprecipitated from A549 cells using antibody LMH 85 and probed with 25H2 [a commercial β-chain binding mAb] (left panel)
Figure 1:
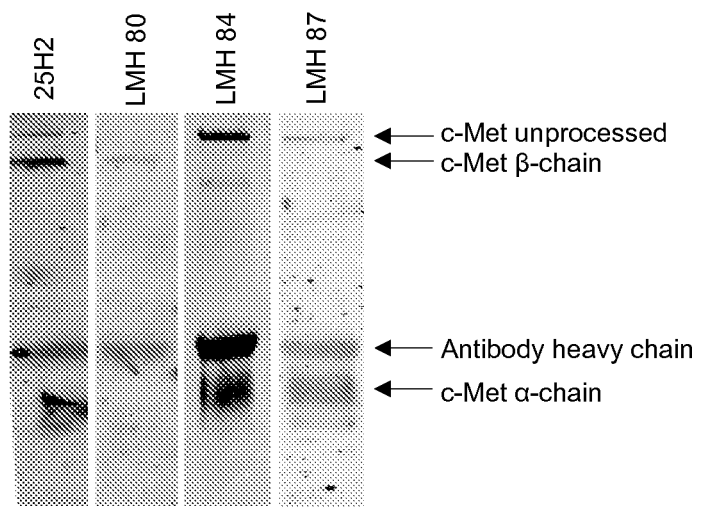
Figure 1:
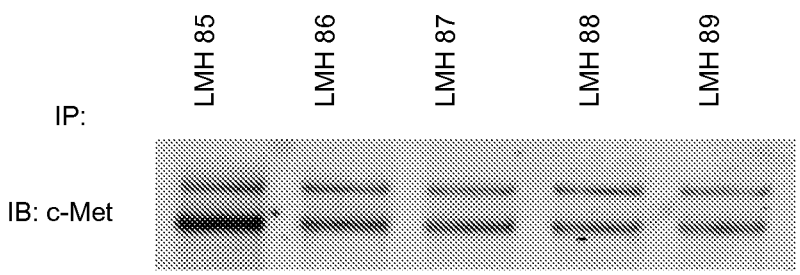
Figure 1:
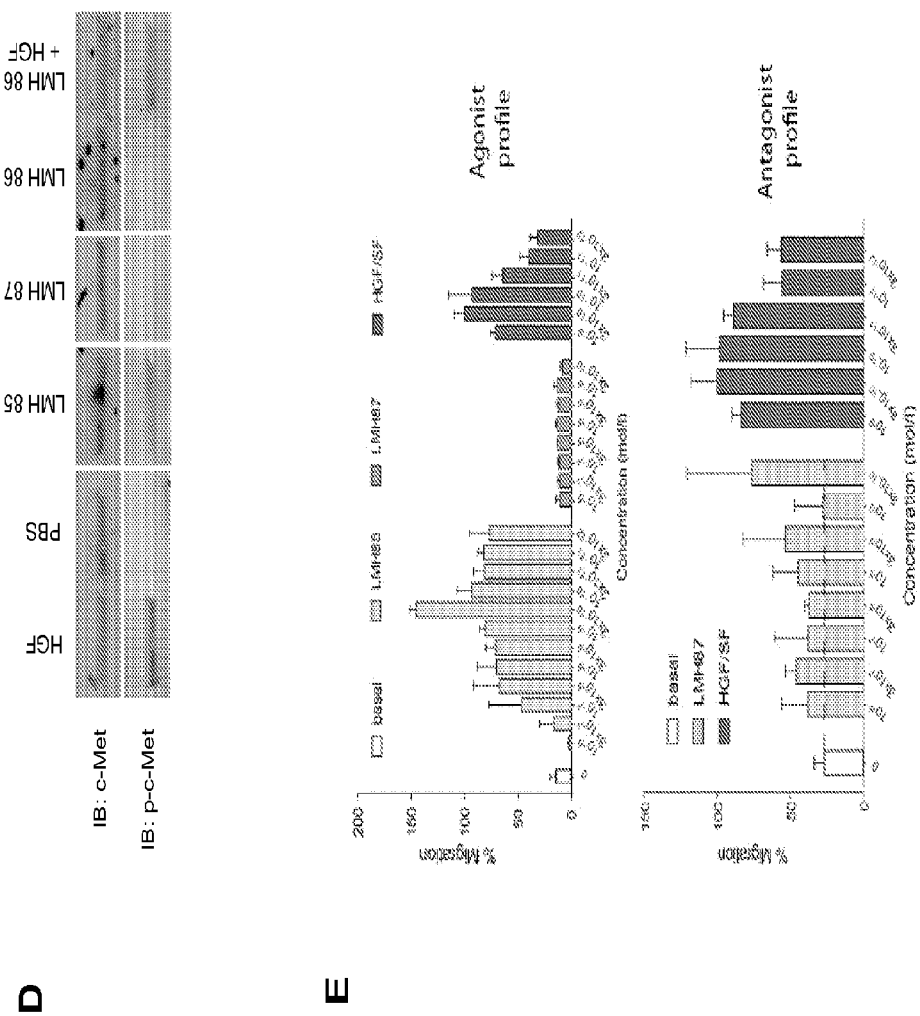

A summary of the characterisation of LMH antibodies 80 to 89 is provided in Table 2. Supernatant from LMH clones were initially screened by ELISA assay as described in Materials and Methods for specific reactivity with recombinant truncated c-Met antigen. Positive supernatants were then screened for binding to c-Met receptor on A549 cells by flow cytometry. The results of these analyses are shown in Table 2. A representative FACS analysis showing binding of antibodies LMH 85 and LMH 87 against an isotype matched control is shown in FIG. 1A.

TABLE 2

Characterisation of LMH antibodies

| Antibody | ELISA positive | Flow Cytometry positive | Immunoblot | Immuno precipitation | Binding affinity ($K_D$) | c-Met Antagonist^ | c-Met Agonist^ | HGF-induced cell migration antagonist * | Antibody induced cell migration agonist * |
|---|---|---|---|---|---|---|---|---|---|
| LMH 80 | Yes | Yes | Yes, β-chain | Yes, unprocessed c-Met | 34 nM | No | No | n.d | n.d |
| LMH 81 | Yes | Yes | No | Yes unprocessed c-Met | 12 nM | No | No | n.d | n.d |
| LMH 82 | Yes | Yes | Yes, α-chain | Yes unprocessed c-Met | n.d. | No | No | n.d | n.d |
| LMH 83 | Yes | Yes | No | No | 26 nM | No | No | No | No |
| LMH 84 | Yes | Yes | Yes, α-chain | Yes | 36 nM | No | No | No | No |
| LMH 85 | Yes | Yes | No | Yes | n.d. | No | Yes | No | Yes |
| LMH 86 | Yes | Yes | Yes, α-chain | Yes | n.d. | No | No | No | No |
| LMH 87 | Yes | Yes | Yes, α-chain | Yes | 2.6 nM | No | No | Yes | No |
| LMH 88 | Yes | Yes | Yes, α-chain | Yes | 76 nM | No | No | Yes | No |
| LMH 89 | Yes | Yes | Yes, α-chain | Yes | 31 nM | No | No | Yes | No |

* Assay performed in SK-OV-3 cells
^ Assay performed in A549 cells
n.d Not determined The reactivity of the antibodies was examined by immunoblot/Western blot analysis. Total c-Met was immunoprecipitated from A549 cells and probed with 25H2 a commercial antibody which binds to the beta (β) chain of c-Met and antibodies LMH 80, 82, 84 and 86 to 89. The results of this analysis is provided in FIG. 1B (for antibodies LMH 80, LMH 84 and LMH87) and in Table 2. Antibodies LMH 82, 84, 86, 87, 88 and 89 bound the alpha chain of c-Met while LMH 80 specifically bound the beta chain (representative blot shown for antibodies LMH 80, LMH 84 and LMH 87 in FIG. 1B).

In further confirmatory experiments, the c-Met from LoVo cells was immunoprecipitated by antibodies LMH 80, 81, 82 or 85 and western blotted with 25H2 that recognises the beta chain of c-Met in both the unprocessed and processed forms of the receptor. This data supported that seen with A549 cells in that antibodies LMH 80, 81 and 82 recognised the unprocessed form of c-Met (not shown).

Immunoprecipitation studies showed that antibodies LMH 80, 81, 82 and 84-89 were capable of c-Met immunoprecipitation. FIG. 1C shows a representative immunoblot for LMH antibodies LMH 85, LMH 86, LMH 87, LMH 88 and LMH 89.

The agonist/antagonist activity of selected LMH antibodies was examined by immunoblot as shown in FIG. 1D. A459 cells were treated with either antibody alone or antibody in the presence of HGF ligand and whole cell lysates prepared. Antibody LMH 85 was found to promote c-Met phosphorylation and therefore act as an agonist of c-Met. Antibodies LMH 86 and 87 has no effect on c-Met phosphorylation. Furthermore, antibody LMH 86 was unable to block HGF stimulated c-Met phosphorylation. The agonist/antagonist activities of the antibodies are summarised in Table 2.

The binding affinity of the LMH antibodies was determined by BIAcore analysis. The dissociation constants are shown in Table 2.

Example 3

Antibody LMH 85 and LMH 87 Agonist and Antagonist Profile

Antibody LMH 85 was able to induce migration in SK-OV-3 cells (FIG. 1E, top panel), consistent with its ability to induce phosphorylation of c-Met. In contrast LMH 87 alone had no effect on cell migration (FIG. 1E, top panel), confirming its lack of agonist activity. In contrast however, antibody LMH 87 was able to significantly inhibit HGF/SF induced migration of SK-OV3 cells (FIG. 1E, bottom panel, p<0.05). This data confirms that antibody LMH 87 is an antagonist of c-Met.

These results are consistent with the biochemical data. LMH 85 activation of c-Met results in increased migration, while LMH 87, which has no effect on c-Met activation, has no effect on cell migration.

As shown in FIG. 1f, the negative control showed no cell migration stimulation, while HGF stimulated cell migration. When HGF was mixed with LMH 87, a consistent reduction n cell migration was observed for all concentrations used (approximately 60% less cell migration). This indicates that LMH 87 is a c-Met antagonist.

Example 4

Further Characterisation of LMH Antibodies

LMH antibodies 80 to 82 and 85 were further characterised for binding to c-Met as shown in FIG. 2. Under reducing conditions the unprocessed form of c-Met remains intact while the processed form is reduced to alpha and beta chains. Accordingly, if LMH 80-82 bound the processed c-Met then the beta chain should be present in the immunoblot. As demonstrated in FIG. 2, LMH antibodies LMH 80-82 only bound the unprocessed form of the receptor on the cell surface. In contrast, antibody LMH85 was found to immunoprecipitate both unprocessed c-Met and processed c-Met as evidenced by the presence of the beta chain.

FIG. 3 further demonstrates that antibodies LMH 80-82 recognise unprocessed c-Met. LoVo colon cancer cells predominantly express unprocessed c-Met. LMH 80 and 81 show strong binding to these cells as evidenced by flow cytometry analysis. U87MG cells express mostly unprocessed c-Met and low amounts of unprocessed receptor. LMH 80 to 82 bound weakly to these cells compared with antibody LMH 85, confirming that they recognise the unprocessed form of c-Met.

Example 5

Epitope Mapping of LMH Antibodies

Epitope mapping of the LMH antibodies was carried out as described in Materials and Methods. The reactivity of an antibody to a given 20 mer peptide was determined by ELISA assays and the results for representative antibodies LMH 80, LMH 82 and LMH 87 is shown in FIG. 4 (A-C). The peptide sequence bound by each antibody was aligned to determine the core epitope.

Antibody LMH 80 recognised an epitope having a core amino acid sequence RHFQSCSQCLSAPPF (SEQ ID NO:6) located at amino acids 521 to 535 of the c-Met sequence.

Antibody LMH 81 recognised an epitope having a core amino acid sequence RHFQSCSQCLSAPPFVQCGW (SEQ ID NO:5) located at amino acids 521 to 541 of the c-Met sequence.

Antibody LMH 82 recognised an epitope having a core amino acid sequence VVDTYYDDQL (SEQ ID NO:2) located at amino acids 121 to 130 of the c-Met sequence.

Antibody LMH 87 recognised an epitope having a core amino acid sequence DVLPEFRDSY (SEQ ID NO:4). This core epitope was also recognised by antibodies LMH 86, LMH 88 and LMH 89 located at amino acids 236 to 245 of the c-Met sequence.

Antibody LMH 84 recognised an epitope having a core amino acid sequence VRRLKETKDGFMFLT (SEQ ID NO:3) located at amino acids 216 to 230 of the c-Met sequence.

Example 6

Amino Acid Sequences of the LMH Antibodies

The amino acid sequence of the variable heavy and light chains for LMH 85 and LMH 87 was determined by standard procedures as described in Materials and Methods. The complementarity determining regions (CDRs) for antibodies LMH85 and LMH87 are indicated below.

The CDR sequences are as follows:

| Heavy chain CDRs LMH 80 | |
|---|---|
| LMH 80 $V_H$ CDR1 | GYTFTDNS (SEQ ID NO: 7) |
| LMH 80 $V_H$ CDR2 | VNTETGEP (SEQ ID NO: 8) |
| LMH 80 $V_H$ CDR3 | ARDGHYFAY (SEQ ID NO: 9) |
| Light chain CDRs LMH 80 | |
| LMH 80 $V_L$ CDR1 | QSLLYSSNQKDY (SEQ ID NO: 10) |
| LMH 80 $V_L$ CDR2 | WAS (SEQ ID NO: 11) |
| LMH 80 $V_L$ CDR3 | QQYYSYPLT (SEQ ID NO: 12) |
| Heavy chain CDRs LMH 82 | |
| LMH 82 $V_H$ CDR1 | GYTFTDYY (SEQ ID NO: 15) |
| LMH 82 $V_H$ CDR2 | INPNNGGT (SEQ ID NO: 16) |
| LMH 82 $V_H$ CDR3 | ARSGY (SEQ ID NO: 17) |
| Light chain CDRs LMH 82 | |
| LMH 82 $V_L$ CDR1 | QSILHSNGNTY (SEQ ID NO: 18) |
| LMH 82 $V_L$ CDR2 | KVS (SEQ ID NO: 19) |
| LMH 82 $V_L$ CDR3 | FQGSHVPWT (SEQ ID NO: 20) |
| Heavy chain CDRs LMH 85 | |
| LMH 85 $V_H$ CDR1 | GYTFIIYW (SEQ ID NO: 31) |
| LMH 85 $V_H$ CDR2 | INPSNDYT (SEQ ID NO: 32) |
| LMH 85 $V_H$ CDR3 | ARDSYDYDDGAYAMDY (SEQ ID NO: 33) |
| Light chain CDRs LMH 85 | |
| LMH 85 $V_L$ CDR1 | SGVNY (SEQ ID NO: 34) |
| LMH 85 $V_L$ CDR2 | ATS (SEQ ID NO: 35) |
| LMH 85 $V_L$ CDR3 | QQWISHPFT (SEQ ID NO: 36) |
| Heavy chain CDRs LMH 87 | |
| LMH 87 $V_H$ CDR1 | GNTLKDDH (SEQ ID NO: 23) |
| LMH 87 $V_H$ CDR2 | IYPGGGRT (SEQ ID NO: 24) |
| LMH 87 $V_H$ CDR3 | TNLVFDV (SEQ ID NO: 25) |
| Light chain CDRs LMH 87 | |
| LMH 87 $V_L$ CDR1 | KSLLHSNGNTY (SEQ ID NO: 26) |
| LMH 87 $V_L$ CDR2 | RMS (SEQ ID NO: 27) |
| LMH 87 $V_L$ CDR3 | MQNLEYPFT (SEQ ID NO: 28) |

Example 7

Antagonist Activity of Single Chain (scFv) Fragments

A549 cells were treated with 50 μg/ml of either scFv 85 or scFv 87 for 1 h and then HGF added. Whole cell lysates were then prepared and probed for either total c-Met, phosphorylated c-Met (Tyr1234/1235) and (Tyr1230/1234/1235) or a pan-actin antibody to control for loading. Both phosphorylated c-Met blots show that scFv 85, but not scFv 87, blocks HGF stimulation of c-Met (see FIG. 5). Therefore, the scFv LMH 85 appears to act as an antagonist of HGF stimulation of c-Met. This function is markedly different from the intact LMH 85 antibody which is an agonist of the c-Met receptor.

Example 8

LMH 87 Downregulates Total Surface c-Met and Inhibits Tumor Cell Growth

Antibody LMH 87 was tested for is ability to down-regulate c-Met in A549 lung cancer cells by treating them with antibody for 8 or 24 hours. LMH 87 was able to down-regulate surface c-Met in A549 cells (FIG. 6A, upper panel) by 40% (FIG. 6A, lower bar graph) and total cellular c-Met by a similar amount (FIG. 6A, lower blot). LMH 87 also reduced total c-Met in U87MG glioma cells (FIG. 6B) by 50% as determined by densitometry (FIG. B, bar graph).

Untreated or PBS treated controls show similar total amounts of c-Met but cells treated with LMH 87 show a reduction in total c-Met in both cell lines. Accordingly, LMH 87 was found to cause c-Met receptor downregulation. Thus, this data demonstrates that c-Met is removed from the surface of A549 cells.

Antibodies LMH 86, 88 and 89 bind to the same core epitope as antibody LMH 87, but LMH 88 was the only other antibody to reduce total c-Met levels; like antibody LMH 87 down-regulation of the c-Met receptor was sustained for at least 24 hours (FIG. 6A).

Example 9

Antibody LMH 87 Inhibition of Cell Growth in Vitro and in Vivo

In FIG. 7A, an xCELLigence™ analysis of A549 cells treated with LMH 87 was performed in vitro. The xCELLigence system facilitates the analysis of cells in real time in response to a given stimulus. A459 cells were treated with either PBS, or multiple doses of antibody LMH 87; 10 μg/ml, 50 μg/ml, and 100 μg/ml as indicated in FIG. 7A. Both the 50 and 100 μg/ml treatment groups caused a significant decrease in cell index compared to the PBS control group, consistent with inhibition of cell growth.

Antibody LMH 87 was also capable of significantly inhibiting tumor growth in a mouse xenograft model. The results of U87MG xenografts in mice treated with LMH 87 is shown in FIG. 7B. LMH 87 significantly inhibited tumor growth at day 12 (p=0.014) and day 14 (p=0.03).

Discussion

The present inventors have identified a range of antibodies that bind to c-Met and which will be useful for treating cancer. Three of the antibodies, LMH 80, 81 and 82 are unique in being able to preferentially bind the unprocessed form of c-Met on the surface of cancer cells. This property makes these antibodies tumor specific and as such makes them ideal for delivering compounds such as cytotoxics, radioisotopes and siRNA to the tumor cells. Of these antibodies, LMH 80 was specific for the beta chain of c-Met and LMH 82 was specific for the alpha chain of c-met.

Another antibody identified by the inventors, antibody LMH 85 was found to be an agonist of c-Met and appears to recognise a conformational epitope present on c-Met. Interestingly, an scFV based on this antibody was found to block HGF activation of c-Met and therefore exhibit antagonist activity.

Antibodies LMH 86, LMH 87, LMH 88 and LMH 89 were all found to recognise the same core epitope sequence on the alpha chain of c-Met. A representative antibody from this group LMH was demonstrated to bind cancer cells and cause c-Met receptor downregulation/degradation directly, leading to inhibition of tumor growth demonstrated both in vitro and in vivo. A further representative antibody, LMH 88 was also found to cause c-Met receptor down regulation/degradation.

REFERENCES

Birchmeier C, Birchmeier W, Gherardi E, Vande Woude G F: Met, metastasis, motility and more. *Nat Rev Mol Cell Biol* 2003, 4:915-925.

Burgess T, Coxon A, Meyer S, Sun J, Rex K, Tsuruda T, Chen Q, Ho S Y, Li L, Kaufman S, et al: Fully human monoclonal antibodies to hepatocyte growth factor with therapeutic potential against hepatocyte growth factor/c-Met-dependent human tumors. *Cancer Res* 2006, 66:1721-1729.

Comoglio P M, Giordano S, Trusolino L: Drug development of MET inhibitors: targeting oncogene addiction and expedience. *Nat Rev Drug Discov* 2008, 7:504-516.

Doo-Sik Kong et al.: Prognostic significance of c-Met expression in glioblastomas. *Cancer* 2009, 115:140-148.

Eder J P, Vande Woude G F, Boerner S A, LoRusso P M: Novel Therapeutic Inhibitors of the c-Met Signaling Pathway in Cancer. *Clin Cancer Res* 2009, 15:2207-2214.

Engelman J A, Zejnullahu K, Mitsudomi T, Song Y, Hyland C, Park J O, Lindeman N, Gale, C-M, Zhao, X, Christensen J, Kosaka, T, Holmes, A J, Rogers, A M, Cappuzzo F, Mok T, Lee, C, Johnson B E, Cantley L C, Janne P A. MET amplication leads to gefitinib resistance in lung cancer by activating ERBB3 signaling. *Science* 2007, 316:1039-1043.

Faletto D. L., Tsarfaty, I., Kmiecik, T. E., Gonzatti, M., Suzuki, T., and Vande Woude, G. F. (1992). Evidence for non-covalent clusters of the c-met proto-oncogene product. Oncogene 7, 1149-1157.

Gentile A., Trusolino, P M Comoglio. The Met tyrosine kinase receptor in development and cancer. *Cancer Metastasis Rev* 27(2008) 85-94.

Gherardi E, Youles M E, Miguel R N, Blundell T L, Iamele L, Gough J, Bandyopadhyay A, Hartmann G, Butler, P J. Functional map and domain structure of MET, the product of the c-met protoconcogene and receptor for hepatocyte growth factor/scatter factor. *Proc Natl Acad Sci* USA 2003, 100:12039-12044.

Gomes D. A., Rodrigues, M. A., Leite, M. F., Gomez, M. V., Varnai, P., Balla, T., Bennett, A. M., and Nathanson, M. H. (2008). c-Met must translocate to the nucleus to initiate calcium signals. J Biol Chem 283, 4344-4351.

Jagadeeswaran R, Ma P C, Seiwert T Y, Jagadeeswaran S, Zumba O, Nallasura V, Ahmed S, Filiberti R, Paganuzzi M, Puntoni R, Kratzke R A, Gordon G J, Sugarbaker D J, Bueno R, Janamanchi V, Bindokas V P, Kindler H L, Salgia R. Functional analysis of c-Met/hepatocyte growth factor pathway in malignant pleural mesothelioma. Cancer Res 2006 Jan. 1; 66(1):352-61.

Knudsen B S, P Zhao, J Resau, S Cottingham, E Gherardi, E Xu, B Berghuis, J Daugherty, T Grabinski, J Toro, T Giambernardi, R S Skinner, M Gross, E Hudson, E Kort, E Lengyel, A Ventura, R A West, Q Xie, R Hay, G Vande Woude, B Cao. A novel multipurpose monoclonal antibody for evaluating human c-Met expression in preclinical and clinical settings. *Appl Immunohistochem Mol Morphol* vol 17(2009) 57-67.

Komada M., Hatsuzawa, K., Shibamoto, S., Ito, F., Nakayama, K., and Kitamura, N. (1993). Proteolytic processing of the hepatocyte growth factor/scatter factor receptor by furin. FEBS Letters 328, 25-29.

Ma P C, G. Maulik, J. Christensen, R. Salgia. C-Met:structure, functions and potential for therapeutic inhibition. *Cancer Metastasis Rev.* 22(2003) 309-325.

Ma P C, Kijima T, Maulik G, Fox E A, Sattler M, Griffin J D, Johnson B E and Salgia R. c-Met mutational analysis in small cell lung cancer:novel juxtamembrane domain mutations regulating cytoskeletal functions. *Cancer Res* 2003 Pct 1:63(19):6272-81.

Martens T, Schmidt N O, Eckerich C, Fillbrandt R, Merchant M, Schwall R, Westphal M, Lamszus K: A novel one-armed anti-c-Met antibody inhibits glioblastoma growth in vivo. *Clin Cancer Res* 2006, 12:6144-6152.

McLendon R et al., Comprehensive genomic characterisation defines human glioblastoma genes and core pathways. *Nature* 2008 455:1061-1068.

Mizuno K., Higuchi, O., Tajima, H., Yonemasu, T., and Nakamura, T. (1993). Cell density-dependent regulation of hepatocyte growth factor receptor on adult rat hepatocytes in primary culture. J Biochem 114, 96-102.

Mondino A., Giordano, S., and Comoglio, P. M. (1991). Defective posttranslational processing activates the tyrosine kinase encoded by the MET proto-oncogene (hepatocyte growth factor receptor). Mol Cell Biol 11, 6084-6092.

Nieba L et al., BIAcore analysis of histidine-tagged proteins using a chelating NTA sensor chip. *Analytical Biochemistry* 1997, 252:217-228.

Petrelli A, Circosta P, Granziero L, Mazzone M, Pisacane A, Fenoglio S, Comoglio P M, Giordano S. Ab-induced ectodomain shedding mediates hepatocyte growth factor receptor down-regulation and hampers biological activity. *Proc Natl Acad Sci USA* 2006, 103:5090-5095.

Pillay V, Allaf L, Wilding A L, Donoghue J F, Court N W, Greenall S A, Scott A M, Johns T G: The plasticity of oncogene addiction: implications for targeted therapies directed to receptor tyrosine kinases. *Neoplasia* 2009, 11:448-458.

Prat M, Crepaldi T, Pennacchietti S, Bussolino, F, Comoglio P M. Agonistic monoclonal antibodies against the Met receptor dissect the biological responses to HGF. *J Cell Sci* 1998 111 (pt 2):237-247.

Puri N, Ahmed S, Janamanchi V, Tretiakova, M, Zumba O, Krausz T, Jagadeeswaran R and Salgia R. c-Met is a potentially new therapeutic target treatment for human melanoma. *Cancer Research* 2007 Apr. 1; 13(7):2246-53.

Rodrigues G. A., Naujokas, M. A., and Park, M. (1991). Alternative splicing generates isoforms of the met receptor tyrosine kinase which undergo differential processing. Mol Cell Biol 11, 2962-2970.

Rong S., Bodescot, M., Blair, D., Dunn, J., Nakamura, T., Mizuno, K., Park, M., Chan, A., Aaronson, S., and Vande Woude, G. F. (1992). Tumorigenicity of the met proto-oncogene and the gene for hepatocyte growth factor. Mol Cell Biol 12, 5152-5158.

Stellrecht C M and V Gandhi. MET receptor tyrosine kinase as a therapeutic anticancer target. *Cancer Letters* 280 (2009) 1-14.

Tseng J R et al., (2008) J Nucl Med 49(1):129-134

Van der Horst E H, Chinn L, wang M, Velilla T, Tran H, Madrona Y, Lam A, ji M, Hoey T C and Sato A K. Discovery of fully human anti-MET monoclonal antibodies with anti-tumor activity against colon cancer tumor models in vivo. *Neoplasia* 2009, 11:355-364.

The invention claimed is:

1. An isolated antibody or antigen-binding fragment thereof that specifically binds to c-Met on a tumor cell wherein the antibody or fragment comprises an immunoglobulin heavy chain variable region amino acid sequence comprising the complementarity determining region (CDR) sequences SEQ ID NO:23, SEQ ID NO:24 and SEQ ID NO:25 and an immunoglobulin light chain variable region amino acid sequence comprising the complementarity determining region (CDR) sequences SEQ ID NO:26, SEQ ID NO:27 and SEQ ID NO:28.

2. The isolated antibody or antigen-binding fragment thereof according to claim 1 which comprises an immunoglobulin heavy chain comprising a variable region amino acid sequence which is at least 90% identical to SEQ ID NO:29, wherein the antibody specifically binds c-Met.

3. The isolated antibody or antigen-binding fragment thereof according to claim 1 which comprises an immunoglobulin light chain comprising a variable region amino acid sequence which is at least 90% identical to SEQ ID NO:30, wherein the antibody specifically binds c-Met.

4. The isolated antibody or antigen-binding fragment thereof according to claim 1, comprising an immunoglobulin heavy chain comprising a variable region amino acid sequence set forth in SEQ ID NO:29 and an immunoglobulin light chain comprising a variable region amino acid sequence set forth in SEQ ID NO:30.

5. The antigen-binding fragment according to claim 1, which is an scFv.

6. The antibody or antigen-binding fragment thereof according to claim 1 that specifically binds to c-Met on a tumor cell and induces downregulation of the receptor in the absence of c-Met receptor activation, wherein the epitope comprises the amino acid sequence DVLPEFRDSY (SEQ ID NO:4) and wherein the antibody is not a Met4 antibody produced by the hybridoma cell line deposited with the ATCC under Accession No. PTA-7680.

7. The antibody according to claim 1, comprising an immunoglobulin heavy chain comprising a variable region amino acid sequence set forth in SEQ ID NO:29 and an immunoglobulin light chain comprising a variable region amino acid sequence set forth in SEQ ID NO:30.

8. The antibody according to claim 1 having a binding affinity ($K_D$) for c-Met of about 3 nM.

9. A method of inhibiting cellular proliferation of a tumor cell expressing c-Met in a subject, comprising administering to the subject an antibody or antigen binding fragment thereof according to claim 1.

10. The method according to claim 9, wherein the antigen-binding fragment is an scFv.

11. The antibody or antigen-binding fragment thereof according to claim 1 conjugated to an agent.

12. The antibody or antigen-binding fragment thereof according to claim 11, conjugated to an agent selected from a detectable or functional label, or therapeutic agent selected from a cytotoxin or anti-neoplastic agent.

13. An isolated nucleic acid sequence encoding an antibody or antigen-binding fragment according to claim 1.

14. The nucleic acid sequence according to claim 13, wherein the sequence comprises the heavy chain variable region sequence of SEQ ID NO:39 and the light chain variable region sequence of SEQ ID NO:40.

15. A vector comprising an isolated nucleic acid sequence according to claim 14.

16. A host cell comprising the vector according to claim 15.

17. A pharmaceutical composition comprising an antibody or antigen-binding fragment according to any one of claims 1 to 4 or an antibody conjugate according to claim 11 together with a pharmaceutically acceptable carrier or excipient.

18. The pharmaceutical composition according to claim 17 further comprising an anti-cancer agent or therapeutic, an inhibitor of angiogenesis, or an immune modulator.

19. A method of treating undesirable tumor cell proliferation in a subject wherein the tumor cell expresses c-Met which comprises administering to said subject a therapeutically effective amount of an antibody or antigen-binding fragment thereof according to any one of claims 1 to 4 or a conjugate according to claim 11.

20. A method for detecting cells expressing c-Met in a subject, the method comprising contacting the subject, or a sample obtained therefrom, with an antibody or antigen-binding fragment according to any one of claims 1 to 4 or a conjugate according to claim 11 and analysing the subject or sample for binding between human c-Met and the antibody or conjugate, wherein binding detects cells expressing c-Met.

* * * * *

```
                       SEQUENCE LISTING

<160> NUMBER OF SEQ ID NOS: 50

<210> SEQ ID NO 1
<211> LENGTH: 555
<212> TYPE: PRT
<213> ORGANISM: Artificial Sequence
<220> FEATURE:
<223> OTHER INFORMATION: sequence of residues 1-567 of human c-Met

<400> SEQUENCE: 1

Glu Thr Arg Glu Cys Lys Glu Ala Leu Ala Lys Ser Glu Met Asn Val
1               5                   10                  15

Asn Met Lys Tyr Gln Leu Pro Asn Phe Thr Ala Glu Thr Pro Ile Gln
            20                  25                  30

Asn Val Ile Leu His Glu His His Ile Phe Leu Gly Ala Thr Asn Tyr
        35                  40                  45

Ile Tyr Val Leu Asn Glu Glu Asp Leu Gln Lys Val Ala Glu Tyr Lys
    50                  55                  60

Thr Gly Pro Val Leu Glu His Pro Asp Cys Phe Pro Cys Gln Asp Cys
65                  70                  75                  80

Ser Ser Lys Ala Asn Leu Ser Gly Gly Val Trp Lys Asp Asn Ile Asn
                85                  90                  95

Met Ala Leu Val Val Asp Thr Tyr Tyr Asp Asp Gln Leu Ile Ser Cys
            100                 105                 110

Gly Ser Val Asn Arg Gly Thr Cys Gln Arg His Val Phe Pro His Asn
        115                 120                 125

His Thr Ala Asp Ile Gln Ser Glu Val His Cys Ile Phe Ser Pro Gln
    130                 135                 140

Ile Glu Glu Pro Ser Gln Cys Pro Asp Cys Val Val Ser Ala Leu Gly
145                 150                 155                 160

Ala Lys Val Leu Ser Ser Val Lys Asp Arg Phe Ile Asn Phe Phe Val
                165                 170                 175

Gly Asn Thr Ile Asn Ser Ser Tyr Phe Pro Asp His Pro Leu His Ser
            180                 185                 190

Ile Ser Val Arg Arg Leu Lys Glu Thr Lys Asp Gly Phe Met Phe Leu
```

```
                195                 200                 205
Thr Asp Gln Ser Tyr Ile Asp Val Leu Pro Glu Phe Arg Asp Ser Tyr
210                 215                 220

Pro Ile Lys Tyr Val His Ala Phe Glu Ser Asn Asn Phe Ile Tyr Phe
225                 230                 235                 240

Leu Thr Val Gln Arg Glu Thr Leu Asp Ala Gln Thr Phe His Thr Arg
                245                 250                 255

Ile Ile Arg Phe Cys Ser Ile Asn Ser Gly Leu His Ser Tyr Met Glu
                260                 265                 270

Met Pro Leu Glu Cys Ile Leu Thr Glu Lys Arg Lys Arg Ser Thr
                275                 280                 285

Lys Lys Glu Val Phe Asn Ile Leu Gln Ala Ala Tyr Val Ser Lys Pro
290                 295                 300

Gly Ala Gln Leu Ala Arg Gln Ile Gly Ala Ser Leu Asn Asp Asp Ile
305                 310                 315                 320

Leu Phe Gly Val Phe Ala Gln Ser Lys Pro Asp Ser Ala Glu Pro Met
                325                 330                 335

Asp Arg Ser Ala Met Cys Ala Phe Pro Ile Lys Tyr Val Asn Asp Phe
                340                 345                 350

Phe Asn Lys Ile Val Asn Lys Asn Asn Val Arg Cys Leu Gln His Phe
                355                 360                 365

Tyr Gly Pro Asn His Glu His Cys Phe Asn Arg Thr Leu Leu Arg Asn
370                 375                 380

Ser Ser Gly Cys Glu Ala Arg Arg Asp Glu Tyr Arg Thr Glu Phe Thr
385                 390                 395                 400

Thr Ala Leu Gln Arg Val Asp Leu Phe Met Gly Gln Phe Ser Glu Val
                405                 410                 415

Leu Leu Thr Ser Ile Ser Thr Phe Ile Lys Gly Asp Leu Thr Ile Ala
                420                 425                 430

Asn Leu Gly Thr Ser Glu Gly Arg Phe Met Gln Val Val Val Ser Arg
                435                 440                 445

Ser Gly Pro Ser Thr Pro His Val Asn Phe Leu Leu Asp Ser His Pro
450                 455                 460

Val Ser Pro Glu Val Ile Val Glu His Thr Leu Asn Gln Asn Gly Tyr
465                 470                 475                 480

Thr Leu Val Ile Thr Gly Lys Lys Ile Thr Lys Ile Pro Leu Asn Gly
                485                 490                 495

Leu Gly Cys Arg His Phe Gln Ser Cys Ser Gln Cys Leu Ser Ala Pro
                500                 505                 510

Pro Phe Val Gln Cys Gly Trp Cys His Asp Lys Cys Val Arg Ser Glu
                515                 520                 525

Glu Cys Leu Ser Gly Thr Trp Thr Gln Gln Ile Cys Leu Pro Ala Ile
                530                 535                 540

Tyr Lys Ala Asp Leu His His His His His
545                 550                 555

<210> SEQ ID NO 2
<211> LENGTH: 10
<212> TYPE: PRT
<213> ORGANISM: Artificial Sequence
<220> FEATURE:
<223> OTHER INFORMATION: epitope sequence of antibody LHM-82

<400> SEQUENCE: 2

Val Val Asp Thr Tyr Tyr Asp Asp Gln Leu
```

<210> SEQ ID NO 3
<211> LENGTH: 15
<212> TYPE: PRT
<213> ORGANISM: Artificial Sequence
<220> FEATURE:
<223> OTHER INFORMATION: epitope sequence of LMH-84

<400> SEQUENCE: 3

Val Arg Arg Leu Lys Glu Thr Lys Asp Gly Phe Met Phe Leu Thr
1               5                   10                  15

<210> SEQ ID NO 4
<211> LENGTH: 10
<212> TYPE: PRT
<213> ORGANISM: Artificial Sequence
<220> FEATURE:
<223> OTHER INFORMATION: epitope sequence of LMH-86, LMH-87, LMH-88 and
      LMH-89

<400> SEQUENCE: 4

Asp Val Leu Pro Glu Phe Arg Asp Ser Tyr
1               5                   10

<210> SEQ ID NO 5
<211> LENGTH: 20
<212> TYPE: PRT
<213> ORGANISM: Artificial Sequence
<220> FEATURE:
<223> OTHER INFORMATION: epitope sequence of LMH-81

<400> SEQUENCE: 5

Arg His Phe Gln Ser Cys Ser Gln Cys Leu Ser Ala Pro Pro Phe Val
1               5                   10                  15

Gln Cys Gly Trp
            20

<210> SEQ ID NO 6
<211> LENGTH: 15
<212> TYPE: PRT
<213> ORGANISM: Artificial Sequence
<220> FEATURE:
<223> OTHER INFORMATION: epitope sequence of LMH-80

<400> SEQUENCE: 6

Arg His Phe Gln Ser Cys Ser Gln Cys Leu Ser Ala Pro Pro Phe
1               5                   10                  15

<210> SEQ ID NO 7
<211> LENGTH: 8
<212> TYPE: PRT
<213> ORGANISM: Artificial sequence
<220> FEATURE:
<223> OTHER INFORMATION: CDRH1 of LMH-80

<400> SEQUENCE: 7

Gly Tyr Thr Phe Thr Asp Asn Ser
1               5

<210> SEQ ID NO 8
<211> LENGTH: 8
<212> TYPE: PRT
<213> ORGANISM: Artificial sequence
<220> FEATURE:
<223> OTHER INFORMATION: CDRH2 of LMH-80

```
<400> SEQUENCE: 8

Val Asn Thr Glu Thr Gly Glu Pro
1               5

<210> SEQ ID NO 9
<211> LENGTH: 9
<212> TYPE: PRT
<213> ORGANISM: Artificial sequence
<220> FEATURE:
<223> OTHER INFORMATION: CDRH3 of LMH-80

<400> SEQUENCE: 9

Ala Arg Asp Gly His Tyr Phe Ala Tyr
1               5

<210> SEQ ID NO 10
<211> LENGTH: 12
<212> TYPE: PRT
<213> ORGANISM: Artificial sequence
<220> FEATURE:
<223> OTHER INFORMATION: CDRL1 of LMH-80

<400> SEQUENCE: 10

Gln Ser Leu Leu Tyr Ser Ser Asn Gln Lys Asp Tyr
1               5                   10

<210> SEQ ID NO 11
<211> LENGTH: 3
<212> TYPE: PRT
<213> ORGANISM: Artificial sequence
<220> FEATURE:
<223> OTHER INFORMATION: CDRL2 of LMH-80

<400> SEQUENCE: 11

Trp Ala Ser
1

<210> SEQ ID NO 12
<211> LENGTH: 9
<212> TYPE: PRT
<213> ORGANISM: Artificial sequence
<220> FEATURE:
<223> OTHER INFORMATION: CDRL3 of LMH-80

<400> SEQUENCE: 12

Gln Gln Tyr Tyr Ser Tyr Pro Leu Thr
1               5

<210> SEQ ID NO 13
<211> LENGTH: 116
<212> TYPE: PRT
<213> ORGANISM: Artificial sequence
<220> FEATURE:
<223> OTHER INFORMATION: Heavy chain variable region sequence of LMH-80

<400> SEQUENCE: 13

Lys Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Asn
            20                  25                  30

Ser Met His Trp Val Lys Gln Ala Pro Gly Lys Gly Leu Lys Trp Met
        35                  40                  45

Gly Trp Val Asn Thr Glu Thr Gly Glu Pro Thr Tyr Ala Asp Asp Phe
    50                  55                  60
```

```
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Asp Gly His Tyr Phe Ala Tyr Trp Gly Gln Gly Thr Leu Val
            100                 105                 110

Thr Val Ser Ala
        115

<210> SEQ ID NO 14
<211> LENGTH: 113
<212> TYPE: PRT
<213> ORGANISM: Artificial sequence
<220> FEATURE:
<223> OTHER INFORMATION: light chain variable region sequence of LMH-80

<400> SEQUENCE: 14

Asp Ile Val Met Ser Gln Ser Pro Ser Ser Leu Thr Val Ser Val Gly
 1               5                   10                  15

Glu Lys Val Ala Met Ser Cys Lys Ser Ser Gln Ser Leu Leu Tyr Ser
             20                  25                  30

Ser Asn Gln Lys Asp Tyr Leu Ala Trp Tyr Gln Lys Pro Gly Gln
         35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Leu Thr Phe Gly Ala Gly Thr Lys Leu Glu Leu
            100                 105                 110

Lys

<210> SEQ ID NO 15
<211> LENGTH: 8
<212> TYPE: PRT
<213> ORGANISM: Artificial sequence
<220> FEATURE:
<223> OTHER INFORMATION: CDRH1 of LMH-82

<400> SEQUENCE: 15

Gly Tyr Thr Phe Thr Asp Tyr Tyr
 1               5

<210> SEQ ID NO 16
<211> LENGTH: 8
<212> TYPE: PRT
<213> ORGANISM: Artificial sequence
<220> FEATURE:
<223> OTHER INFORMATION: CDRH2 of LMH-82

<400> SEQUENCE: 16

Ile Asn Pro Asn Asn Gly Gly Thr
 1               5

<210> SEQ ID NO 17
<211> LENGTH: 5
<212> TYPE: PRT
<213> ORGANISM: Artificial sequence
<220> FEATURE:
<223> OTHER INFORMATION: CDRH3 of LMH-82
```

```
<400> SEQUENCE: 17

Ala Arg Ser Gly Tyr
1               5

<210> SEQ ID NO 18
<211> LENGTH: 11
<212> TYPE: PRT
<213> ORGANISM: Artificial sequence
<220> FEATURE:
<223> OTHER INFORMATION: CDRL1 of LMH-82

<400> SEQUENCE: 18

Gln Ser Ile Leu His Ser Asn Gly Asn Thr Tyr
1               5                   10

<210> SEQ ID NO 19
<211> LENGTH: 3
<212> TYPE: PRT
<213> ORGANISM: Artificial sequence
<220> FEATURE:
<223> OTHER INFORMATION: CDRL2 of LMH-82

<400> SEQUENCE: 19

Lys Val Ser
1

<210> SEQ ID NO 20
<211> LENGTH: 9
<212> TYPE: PRT
<213> ORGANISM: Artificial sequence
<220> FEATURE:
<223> OTHER INFORMATION: CDRL3 of LMH-82

<400> SEQUENCE: 20

Phe Gln Gly Ser His Val Pro Trp Thr
1               5

<210> SEQ ID NO 21
<211> LENGTH: 112
<212> TYPE: PRT
<213> ORGANISM: Artificial sequence
<220> FEATURE:
<223> OTHER INFORMATION: heavy chain variable region sequence of LMH-82

<400> SEQUENCE: 21

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Tyr Met Lys Trp Val Lys Gln Ser His Gly Lys Asn Leu Glu Trp Ile
            35                  40                  45

Gly Asp Ile Asn Pro Asn Asn Gly Gly Thr Asn Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Gly Tyr Trp Gly Gln Gly Thr Thr Leu Thr Val Ser Ser
            100                 105                 110

<210> SEQ ID NO 22
<211> LENGTH: 112
<212> TYPE: PRT
```

<213> ORGANISM: Artificial sequence
<220> FEATURE:
<223> OTHER INFORMATION: light chain variable region sequence of LMH-82.

<400> SEQUENCE: 22

```
Asp Val Leu Met Thr Gln Thr Pro Leu Ser Leu Pro Val Ser Leu Gly
1               5                   10                  15

Asp Gln Ala Ser Ile Ser Cys Arg Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 23
<211> LENGTH: 8
<212> TYPE: PRT
<213> ORGANISM: Artificial Sequence
<220> FEATURE:
<223> OTHER INFORMATION: CDRH1 sequence of antibody LMH-87

<400> SEQUENCE: 23

```
Gly Asn Thr Leu Lys Asp Asp His
1               5
```

<210> SEQ ID NO 24
<211> LENGTH: 8
<212> TYPE: PRT
<213> ORGANISM: Artificial Sequence
<220> FEATURE:
<223> OTHER INFORMATION: CDRH2 sequence of antibody LMH-87

<400> SEQUENCE: 24

```
Ile Tyr Pro Gly Gly Gly Arg Thr
1               5
```

<210> SEQ ID NO 25
<211> LENGTH: 7
<212> TYPE: PRT
<213> ORGANISM: Artificial Sequence
<220> FEATURE:
<223> OTHER INFORMATION: CDRH3 sequence of antibody LMH-87

<400> SEQUENCE: 25

```
Thr Asn Leu Val Phe Asp Val
1               5
```

<210> SEQ ID NO 26
<211> LENGTH: 11
<212> TYPE: PRT
<213> ORGANISM: Artificial Sequence
<220> FEATURE:
<223> OTHER INFORMATION: CDRL1 sequence of antibody LMH-87

<400> SEQUENCE: 26

```
Lys Ser Leu Leu His Ser Asn Gly Asn Thr Tyr
1               5                   10
```

<210> SEQ ID NO 27
<211> LENGTH: 3
<212> TYPE: PRT
<213> ORGANISM: Artificial Sequence
<220> FEATURE:
<223> OTHER INFORMATION: CDRL2 sequence of antibody LMH-87

<400> SEQUENCE: 27

Arg Met Ser
1

<210> SEQ ID NO 28
<211> LENGTH: 9
<212> TYPE: PRT
<213> ORGANISM: Artificial Sequence
<220> FEATURE:
<223> OTHER INFORMATION: CDRL3 sequence of antibody LMH-87

<400> SEQUENCE: 28

Met Gln Asn Leu Glu Tyr Pro Phe Thr
1               5

<210> SEQ ID NO 29
<211> LENGTH: 114
<212> TYPE: PRT
<213> ORGANISM: Artificial Sequence
<220> FEATURE:
<223> OTHER INFORMATION: heavy chain variable region sequence of
      antibody LMH-87

<400> SEQUENCE: 29

Gln Val Gln Leu Gln Gln Ser Gly Pro Glu Leu Val Lys Ser Gly Ala
1               5                   10                  15

Ser Val Lys Met Ser Cys Lys Ala Ser Gly Asn Thr Leu Lys Asp Asp
            20                  25                  30

His Val His Trp Val Lys Gln Arg Pro Gly Gln Gly Leu Glu Trp Ile
        35                  40                  45

Gly Trp Ile Tyr Pro Gly Gly Gly Arg Thr Arg Tyr Asn Glu Lys Phe
    50                  55                  60

Lys Gly Lys Thr Thr Leu Thr Ala Asp Lys Pro Ser Thr Val Asn
65                  70                  75                  80

Met Leu Leu Ser Ser Leu Thr Ser Glu Asp Ser Ala Ile Tyr Phe Cys
                85                  90                  95

Thr Asn Leu Val Phe Asp Val Trp Gly Ala Gly Thr Thr Val Thr Val
                100                 105                 110

Ser Ser

<210> SEQ ID NO 30
<211> LENGTH: 112
<212> TYPE: PRT
<213> ORGANISM: Artificial Sequence
<220> FEATURE:
<223> OTHER INFORMATION: light chain variable region of antibody LMH-87

<400> SEQUENCE: 30

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

```
Pro Gln Val Leu Ile Tyr Arg Met Ser Asn Leu Ala Ser Gly Val Pro
 50                  55                  60

Asp Arg Phe Ser Gly Ser Gly Ser Gly Thr Ala Phe Thr Leu Arg Ile
 65                  70                  75                  80

Arg Arg Val Glu Ala Glu Asp Val Gly Val Tyr Tyr Cys Met Gln Asn
                 85                  90                  95

Leu Glu Tyr Pro Phe Thr Phe Gly Gly Gly Thr Lys Leu Glu Ile Lys
            100                 105                 110
```

```
<210> SEQ ID NO 31
<211> LENGTH: 8
<212> TYPE: PRT
<213> ORGANISM: Artificial Sequence
<220> FEATURE:
<223> OTHER INFORMATION: CDRH1 sequence of antibody LMH-85

<400> SEQUENCE: 31

Gly Tyr Thr Phe Ile Ile Tyr Trp
 1               5
```

```
<210> SEQ ID NO 32
<211> LENGTH: 8
<212> TYPE: PRT
<213> ORGANISM: Artificial Sequence
<220> FEATURE:
<223> OTHER INFORMATION: CDRH2 sequence of antibody LMH-85

<400> SEQUENCE: 32

Ile Asn Pro Ser Asn Asp Tyr Thr
 1               5
```

```
<210> SEQ ID NO 33
<211> LENGTH: 16
<212> TYPE: PRT
<213> ORGANISM: Artificial Sequence
<220> FEATURE:
<223> OTHER INFORMATION: CDRH3 sequence of antibody LMH-85

<400> SEQUENCE: 33

Ala Arg Asp Ser Tyr Asp Tyr Asp Asp Gly Ala Tyr Ala Met Asp Tyr
 1               5                   10                  15
```

```
<210> SEQ ID NO 34
<211> LENGTH: 5
<212> TYPE: PRT
<213> ORGANISM: Artificial Sequence
<220> FEATURE:
<223> OTHER INFORMATION: CDRL1 sequence of antibody LMH-85

<400> SEQUENCE: 34

Ser Gly Val Asn Tyr
 1               5
```

```
<210> SEQ ID NO 35
<211> LENGTH: 3
<212> TYPE: PRT
<213> ORGANISM: Artificial Sequence
<220> FEATURE:
<223> OTHER INFORMATION: CDRL2 sequence of antibody LMH-85

<400> SEQUENCE: 35

Ala Thr Ser
 1
```

```
<210> SEQ ID NO 36
```

```
<211> LENGTH: 9
<212> TYPE: PRT
<213> ORGANISM: Artificial Sequence
<220> FEATURE:
<223> OTHER INFORMATION: CDRL3 sequence of antibody LMH-85.

<400> SEQUENCE: 36

Gln Gln Trp Ile Ser His Pro Phe Thr
1               5

<210> SEQ ID NO 37
<211> LENGTH: 123
<212> TYPE: PRT
<213> ORGANISM: Artificial Sequence
<220> FEATURE:
<223> OTHER INFORMATION: heavy chain variable region sequence of LMH-85

<400> SEQUENCE: 37

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Ile Ile Tyr
            20                  25                  30

Trp Ile His Trp Ile Lys Gln Arg Pro Gly Gln Gly Leu Glu Trp Ile
        35                  40                  45

Gly Tyr Ile Asn Pro Ser Asn Asp Tyr Thr Glu Tyr Asn Gln Lys Phe
    50                  55                  60

Lys Asp Lys Ala Thr Leu Thr Ala Asp Lys Ser Ser Asn Thr Ala Phe
65                  70                  75                  80

Met Gln Leu Ser Ser Leu Thr Ser Glu Asp Ser Ala Val Tyr Tyr Cys
                85                  90                  95

Ala Arg Asp Ser Tyr Asp Tyr Asp Asp Gly Ala Tyr Ala Met Asp Tyr
            100                 105                 110

Trp Gly Gln Gly Thr Ser Val Thr Val Ser Ser
        115                 120

<210> SEQ ID NO 38
<211> LENGTH: 106
<212> TYPE: PRT
<213> ORGANISM: Artificial Sequence
<220> FEATURE:
<223> OTHER INFORMATION: light chain variable region sequence of LMH-85

<400> SEQUENCE: 38

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Gly Val Asn Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ile Ser His Pro Phe Thr
                85                  90                  95

Phe Gly Ser Gly Thr Lys Leu Glu Ile Lys
            100                 105

<210> SEQ ID NO 39
<211> LENGTH: 342
```

<212> TYPE: DNA
<213> ORGANISM: Artificial Sequence
<220> FEATURE:
<223> OTHER INFORMATION: heavy chain variable region of antibody LMH-87

<400> SEQUENCE: 39

```
caggtccagc tgcagcagtc tggacctgag ctggtgaagt ctggggcttc agtgaagatg      60
tcctgcaagg cttctgggaa caccctcaaa gacgaccatg tacactgggt gaagcagagg     120
cctggacagg gccttgagtg gattggatgg atttatcctg gaggtggtag acaaggtac     180 aatgagaagt tcaagggcaa gaccacactg actgcagaca aaccctccag cacagttaac     240
atgttgctca gtagcctgac ctctgaggac tctgcgatct atttctgtac aaacttggtt     300
ttcgatgtct ggggtgcagg gaccacggtc accgtctcct ca                        342
```

<210> SEQ ID NO 40
<211> LENGTH: 336
<212> TYPE: DNA
<213> ORGANISM: Artificial Sequence
<220> FEATURE:
<223> OTHER INFORMATION: light chain variable region sequence of LMH-87

<400> SEQUENCE: 40

```
gatattgtga tgactcaggc tgcaccctct gtacctgtca ctcctggaga gtcagtatcc      60
atctcctgca ggtctagtaa gagtctcctg catagtaatg caacactta cttgtattgg     120 ttcctgcaga ggccaggcca gtctcctcag gtcctgatat atcggatgtc caaccttgcc     180
tcaggagtcc cagacaggtt cagtggcagt gggtcaggaa ctgctttcac actgagaatc     240
agaagagtgg aggctgagga tgtgggtgtt tattactgta tgcaaaatct agaatatcct     300
ttcacattcg agggggggac caagctggaa ataaaa                               336
```

<210> SEQ ID NO 41
<211> LENGTH: 369
<212> TYPE: DNA
<213> ORGANISM: Artificial Sequence
<220> FEATURE:
<223> OTHER INFORMATION: heavy chain variable region sequence of
      antibody LMH-85.

<400> SEQUENCE: 41

```
caggtccagc ttcagcagtc tggggctgaa ctggcaaaac ctggggcctc agtgaagatg      60
tcctgcaagg cttctggcta caccttatc atctactgga ttcactggat aaaacagagg     120
cctggacagg gtctggaatg gattgggtac attaatccta gtaatgacta tactgagtac     180
aatcagaagt tcaaggacaa ggccacattg actgcagaca atcctccaa cacagccttc     240 atgcaactga gcagcctgac atctgaggac tctgcagtct attactgtgc aagagattcc     300
tatgattacg acgacggggc ctatgctatg gactactggg gtcaaggaac ctcagtcacc     360
gtctcctca                                                             369
```

<210> SEQ ID NO 42
<211> LENGTH: 318
<212> TYPE: DNA
<213> ORGANISM: Artificial Sequence
<220> FEATURE:
<223> OTHER INFORMATION: light chain variable region sequence of
      antibody LMH-85

<400> SEQUENCE: 42

```
caaattgttc tctcccagtc tccagcaatc ctgtctgcat ctccagggga gaaggtcact      60
```

```
atgacttgca gggccagctc aggtgtaaat tacatgcact ggtaccagca gaagccagga    120
tcctccccca aaccctggat ttatgccact tccaacctgg cttctggagt ccctgctcgc    180
ttcagtggca gtgggtctgg gacctcttac tctctcacaa tcagcagagt ggaggctgaa    240
gatgctgcca cttattactg ccagcagtgg attagtcacc cattcacgtt cggctcgggg    300
acaaagttgg aaataaaa                                                  318
```

<210> SEQ ID NO 43
<211> LENGTH: 11
<212> TYPE: PRT
<213> ORGANISM: Artificial Sequence
<220> FEATURE:
<223> OTHER INFORMATION: multi-substrate docking site
<220> FEATURE:
<221> NAME/KEY: VARIANT
<222> LOCATION: (5)...(7)
<223> OTHER INFORMATION: Xaa is any amino acid
<400> SEQUENCE: 43

Tyr Val His Val Xaa Xaa Xaa Tyr Val Asn Val
1               5                   10

<210> SEQ ID NO 44
<211> LENGTH: 20
<212> TYPE: PRT
<213> ORGANISM: Artificial Sequence
<220> FEATURE:
<223> OTHER INFORMATION: peptide 104

<400> SEQUENCE: 44

Asn Gly Leu Gly Cys Arg His Phe Gln Ser Cys Ser Gln Cys Leu Ser
1               5                   10                  15

Ala Pro Pro Phe
            20

<210> SEQ ID NO 45
<211> LENGTH: 20
<212> TYPE: PRT
<213> ORGANISM: Artificial Sequence
<220> FEATURE:
<223> OTHER INFORMATION: peptide 23

<400> SEQUENCE: 45

Val Trp Lys Asp Asn Ile Asn Met Ala Leu Val Val Asp Thr Tyr Tyr
1               5                   10                  15

Asp Asp Gln Leu
            20

<210> SEQ ID NO 46
<211> LENGTH: 20
<212> TYPE: PRT
<213> ORGANISM: Artificial Sequence
<220> FEATURE:
<223> OTHER INFORMATION: peptide 24

<400> SEQUENCE: 46

Ile Asn Met Ala Leu Val Val Asp Thr Tyr Tyr Asp Asp Gln Leu Ile
1               5                   10                  15

Ser Cys Gly Ser
            20

<210> SEQ ID NO 47
<211> LENGTH: 20
<212> TYPE: PRT

```
<213> ORGANISM: Artificial Sequence
<220> FEATURE:
<223> OTHER INFORMATION: peptide 25

<400> SEQUENCE: 47

Val Val Asp Thr Tyr Tyr Asp Asp Gln Leu Ile Ser Cys Gly Ser Val
1               5                   10                  15

Asn Arg Gly Thr
            20

<210> SEQ ID NO 48
<211> LENGTH: 20
<212> TYPE: PRT
<213> ORGANISM: Artificial Sequence
<220> FEATURE:
<223> OTHER INFORMATION: peptide 46

<400> SEQUENCE: 48

Phe Met Phe Leu Thr Asp Gln Ser Tyr Ile Asp Val Leu Pro Glu Phe
1               5                   10                  15

Arg Asp Ser Tyr
            20

<210> SEQ ID NO 49
<211> LENGTH: 20
<212> TYPE: PRT
<213> ORGANISM: Artificial Sequence
<220> FEATURE:
<223> OTHER INFORMATION: peptide 47

<400> SEQUENCE: 49

Asp Gln Ser Tyr Ile Asp Val Leu Pro Glu Phe Arg Asp Ser Tyr Pro
1               5                   10                  15

Ile Lys Tyr Val
            20

<210> SEQ ID NO 50
<211> LENGTH: 20
<212> TYPE: PRT
<213> ORGANISM: Artificial Sequence
<220> FEATURE:
<223> OTHER INFORMATION: peptide 48

<400> SEQUENCE: 50

Asp Val Leu Pro Glu Phe Arg Asp Ser Tyr Pro Ile Lys Tyr Val His
1               5                   10                  15

Ala Phe Glu Ser
            20
```